(12) United States Patent
Schwartz et al.

(10) Patent No.: US 8,486,701 B2
(45) Date of Patent: Jul. 16, 2013

(54) ETS2 AND MESP1 GENERATE CARDIAC PROGENITORS FROM FIBROBLASTS

(75) Inventors: Robert J. Schwartz, Houston, TX (US); Vladimir N. Potaman, Houston, TX (US); Jose Francisco Islas, Houston, TX (US)

(73) Assignees: University of Houston, Houston, TX (US); Texas Heart Institute, Houston, TX (US); The Texas A&M University System, College Station, TX (US)

( * ) Notice: Subject to any disclaimer, the term of this patent is extended or adjusted under 35 U.S.C. 154(b) by 0 days.

(21) Appl. No.: 13/040,611

(22) Filed: Mar. 4, 2011

(65) Prior Publication Data

US 2011/0223670 A1    Sep. 15, 2011

Related U.S. Application Data

(60) Provisional application No. 61/339,509, filed on Mar. 5, 2010.

(51) Int. Cl.
| | |
|---|---|
| C12Q 1/68 | (2006.01) |
| C12N 5/10 | (2006.01) |
| C12N 5/071 | (2010.01) |
| C12N 15/00 | (2006.01) |
| C12N 15/87 | (2006.01) |
| C12N 15/74 | (2006.01) |

(52) U.S. Cl.
USPC .......... 435/455; 435/6.13; 435/465; 435/467; 435/476; 435/363; 435/371

(58) Field of Classification Search
None
See application file for complete search history.

(56) References Cited

U.S. PATENT DOCUMENTS

| | | | |
|---|---|---|---|
| 2004/0047845 A1* | 3/2004 | Watson et al. ............. | 424/93.21 |
| 2009/0227032 A1 | 9/2009 | Yamanaka et al. | |

FOREIGN PATENT DOCUMENTS

| | | |
|---|---|---|
| WO | 2010017562 A2 | 2/2010 |

OTHER PUBLICATIONS

Islas et al., Transcription factors ETS2 and MESP1 transdifferentiate human dermal fibroblasts into cardiac progenitors; PNAS, Published online before print Jul. 23, 2012, doi: 10.1073/pnas.1120299109, 2012.*
Steinhauser et al., Regeneration of the heart; EMBO Molecular Medicine, vol. 3, 701-712, 2011.*
European Patent Office; Written Opinion; PCT Application No. PCT/US2011/027160; Feb. 7, 2012.
Bergmann, O. et al. Evidence for cardiomyocyte renewal in humans. Science 324: 5923, 98-102, 2009.
Beh, J. et al. FoxF is essential for FGF-induced migration of heart progenitor cells in the ascidian Ciona intestinalis. Development 134: 3297-3305, 2007.
Davidson, B. Ciona intestinalis as a model for cardiac development. Semin. Cell Dev. Biol. 18: 16-26, 2007.
Yu, J. Induced pluripotent stem cell lines derived from human somatic cells. Science 318:1917-1920, 2007.
Davidson B. and Levine, M. Evolutionary origins of the vertebrate heart: Specification of the cardiac lineage in Ciona intestinalis. Proc. Natl. Acad. Sci. USA 100: 11469-11473.
Imai, K.S., Satoh, N. and Satou, Y. A Twist-like bHLH gene is a downstream factor of an endogenous FGF and determines mesenchymal fate in the ascidian embryos. Development 130: 4461-4472, 2003.
Imai, K.S., Hino, K., Yagi, K., Satoh, N. and Satou, Y. Gene expression profiles of transcription factors and signaling molecules in the ascidian embryo: towards a comprehensive understanding of gene networks. Development 131: 4047-4058, 2004.
Kitajima, S. et al. MesP1 and MesP2 are essential for the development of cardiac mesoderm. Development 127: 3215-3226, 2000.
Moretti, A. et al. Multipotent embryonic isl+ progenitor cells lead to cardiac, smooth muscle and endothelial cell diversification. Cell 127: 1151-1165, 2006.
Park, I.H. et al. Reprogramming of human somatic cells to pluripotency with defined factors. Nature 451: 141-146, 2008.
Saga, Y. et al. MesP1 is expressed in the heart precursor cells and required for the formation of a single heart tube. Development 126:3437-3447, 1999.
Saga, Y., Kitajima, S. and Miyagawa-Tomita, SMesp1 expression is the earliest sign of cardiovascular development. Trends Cardiovasc Med. 10:345-352, 2000.
Takahashi, K. et al. Induction of pluripotent stem cells from adult human fibroblasts by defined factors. Cell 131:861-872, 2007.
European Patent Office; International Search Report and Written Opinion; PCT Application No. PCT/US2011/027160; Jul. 6, 2011.
Bondue A., et al.; Mesp1 acts as a Master Regulator of Multipotent Cardiovascular Progenitor Specification; Cell Stem Cell 3, 69-84, Jul. 2008.
Lindsley, R.C., et al; Mesp1 Coordinately Regulates Cardiovascular Fate Restriction and Epithelial-Mesenchymal Transition in Differentiating ESCs; Cell Stem Cell 3, 55-68, Jul. 2008.
Lie-Venema, H., et al; Ets-1 and Ets-2 Transcription Factors are Essential for Normal Coronary and Myocardial Development in Chicken Embryos; Circulation Research, vol. 92, No. 7, 749-756, Apr. 18, 2003.

* cited by examiner

*Primary Examiner* — Celine Qian
*Assistant Examiner* — Addison D Ault
(74) *Attorney, Agent, or Firm* — Jackson Walker L.L.P.

(57) ABSTRACT

A method for modulating cell differentiation capabilities using heterologous gene expression. Some embodiments of the invention relate to a method for inducing a cardiac progenitor cell by delivering a reprogramming factor to the cell, wherein the reprogramming factor comprises ETS2 or a combination of ETS2 and Mesp1.

3 Claims, 13 Drawing Sheets

SEQUENCE LISTING

<160> NUMBER OF SEQ ID NOS: 86

<210> SEQ ID NO 1
<211> LENGTH: 1820
<212> TYPE: DNA
<213> ORGANISM: Artificial Sequence
<220> FEATURE:
<223> OTHER INFORMATION: human ELK4 gene sequence

<400> SEQUENCE: 1

```
ggagcccgc gcgcggcgtc gctcattgct atggacagtg ctatcaccct gtggcagttc        60
cttcttcagc tcctgcagaa gcctcagaac aagcacatga tctgttggac ctctaatgat       120
gggcagttta agcttttgca ggcagaagag gtggctcgtc tctgggggat tcgcaagaac       180
aagcctaaca tgaattatga caaactcagc cgagccctca gatactatta tgtaaagaat       240
atcatcaaaa aagtgaatgg tcagaagttt gtgtacaagt ttgtctctta tccagagatt       300
ttgaacatgg atccaatgac agtgggcagg attgagggtg actgtgaaag tttaaacttc       360
```

-continued

```
agtgaagtca gcagcagttc caaagatgtg gagaatggag ggaaagataa accacctcag    420
cctggtgcca agacctctag ccgcaatgac tacatacact ctggcttata ttcttcattt    480
actctcaact ctttgaactc ctccaatgta aagcttttca aattgataaa gactgagaat    540
ccagccgaga aactggcaga gaaaaaatct cctcaggagc ccacaccatc tgtcatcaaa    600
tttgtcacga caccttccaa aaagccaccg gttgaacctg ttgctgccac catttcaatt    660
ggcccaagta tttctccatc ttcagaagaa actatccaag ctttggagac attggtttcc    720
ccaaaactgc cttccctgga agccccaacc tctgcctcta acgtaatgac tgcttttgcc    780
accacaccac ccatttcgtc catacccct ttgcaggaac tcccagaac accttcacca    840 ccactgagtt ctcacccaga catcgacaca gacattgatt cagtggcttc tcagccaatg    900
gaacttccag agaatttgtc actggagcct aaagaccagg attcagtctt gctagaaaag    960
gacaaagtaa ataattcatc aagatccaag aaacccaaag ggttagaact ggcacccacc   1020
cttgtgatca cgagcagtga tccaagccca ctgggaatac tgagcccatc tctccctaca   1080
gcttctctta caccagcatt tttttcacag gtagcttgct cgctctttat ggtgtcacca   1140 ttgcttttcat ttatttgccc ttttaagcaa atccagaatt tatacactca agtttgcttt   1200
ctgttactta ggtttgtctt agaaaggtta tgtgtgactg tcatgtgaaa gttaccccat   1260
ttctcatctt aattaggatt gctaaaatag aaagtttgga gtattttctt aaaaaattca   1320
ttgttctaca agtaaataaa tattttgatt tttctatttc ctcctaaaga aagtacacac   1380
actctctcgc tctctctcgg tcttataaaa ctcgttggtg tcttataaaa caaacagtga   1440
taatctcaag ttagaaaaca gtaggtcctg agaaccataa gaaaaatgac tggtgtgatg   1500
ttgagtaaca agttggtaca gttactttag ctatttatta acttgctcat ctcatagaac   1560
attttaatag attttttcaca cacctcatta ttaaaaaaaa acaaacatgc tggtgtcttg   1620
gttacccatt attcctctgt acctgaattc aggttggttt ttctatttgg aaaagacttt   1680
ataaatgttg gcttaaaaag aggttgagca ccagaatctc agaatttacc accaaagaac   1740
tcatccatgt aaccaaaaac cacttgtacc cccaaaaact attgaaataa aaatttaaaa   1800
aattaaaaaa aaaaaaaaaa                                                1820
```

<210> SEQ ID NO 2
<211> LENGTH: 405
<212> TYPE: PRT
<213> ORGANISM: Artificial Sequence
<220> FEATURE:
<223> OTHER INFORMATION: human ELK4 protein sequence

<400> SEQUENCE: 2

```
Met Asp Ser Ala Ile Thr Leu Trp Gln Phe Leu Leu Gln Leu Leu Gln
1               5                   10                  15

Lys Pro Gln Asn Lys His Met Ile Cys Trp Thr Ser Asn Asp Gly Gln
            20                  25                  30

Phe Lys Leu Leu Gln Ala Glu Glu Val Ala Arg Leu Trp Gly Ile Arg
        35                  40                  45

Lys Asn Lys Pro Asn Met Asn Tyr Asp Lys Leu Ser Arg Ala Leu Arg
    50                  55                  60

Tyr Tyr Tyr Val Lys Asn Ile Ile Lys Lys Val Asn Gly Gln Lys Phe
65                  70                  75                  80

Val Tyr Lys Phe Val Ser Tyr Pro Glu Ile Leu Asn Met Asp Pro Met
                85                  90                  95

Thr Val Gly Arg Ile Glu Gly Asp Cys Glu Ser Leu Asn Phe Ser Glu
```

```
            100                 105                 110
Val Ser Ser Ser Ser Lys Asp Val Glu Asn Gly Gly Lys Asp Lys Pro
            115                 120                 125

Pro Gln Pro Gly Ala Lys Thr Ser Ser Arg Asn Asp Tyr Ile His Ser
    130                 135                 140

Gly Leu Tyr Ser Ser Phe Thr Leu Asn Ser Leu Asn Ser Ser Asn Val
145                 150                 155                 160

Lys Leu Phe Lys Leu Ile Lys Thr Glu Asn Pro Ala Glu Lys Leu Ala
                165                 170                 175

Glu Lys Lys Ser Pro Gln Glu Pro Thr Pro Ser Val Ile Lys Phe Val
            180                 185                 190

Thr Thr Pro Ser Lys Lys Pro Pro Val Glu Pro Val Ala Ala Thr Ile
    195                 200                 205

Ser Ile Gly Pro Ser Ile Ser Pro Ser Ser Glu Glu Thr Ile Gln Ala
210                 215                 220

Leu Glu Thr Leu Val Ser Pro Lys Leu Pro Ser Leu Glu Ala Pro Thr
225                 230                 235                 240

Ser Ala Ser Asn Val Met Thr Ala Phe Ala Thr Thr Pro Pro Ile Ser
                245                 250                 255

Ser Ile Pro Pro Leu Gln Glu Pro Pro Arg Thr Pro Ser Pro Pro Leu
            260                 265                 270

Ser Ser His Pro Asp Ile Asp Thr Asp Ile Asp Ser Val Ala Ser Gln
        275                 280                 285

Pro Met Glu Leu Pro Gly Asn Leu Ser Leu Pro Lys Asp Gln Asp
    290                 295                 300

Ser Val Leu Leu Glu Lys Asp Lys Val Asn Asn Ser Arg Ser Lys
305                 310                 315                 320

Lys Pro Lys Gly Leu Glu Leu Ala Pro Thr Leu Val Ile Thr Ser Ser
                325                 330                 335

Asp Pro Ser Pro Leu Gly Ile Leu Ser Pro Ser Leu Pro Thr Ala Ser
            340                 345                 350

Leu Thr Pro Ala Phe Phe Ser Gln Val Ala Cys Ser Leu Phe Met Val
    355                 360                 365

Ser Pro Leu Leu Ser Phe Ile Cys Pro Phe Lys Gln Ile Gln Asn Leu
370                 375                 380

Tyr Thr Gln Val Cys Phe Leu Leu Leu Arg Phe Val Leu Glu Arg Leu
385                 390                 395                 400

Cys Val Thr Val Met
            405

<210> SEQ ID NO 3
<211> LENGTH: 1218
<212> TYPE: DNA
<213> ORGANISM: Artificial Sequence
<220> FEATURE:
<223> OTHER INFORMATION: human ELK4 coding sequence

<400> SEQUENCE: 3
atggacagtg ctatcaccct gtggcagttc cttcttcagc tcctgcagaa gcctcagaac    60
aagcacatga tctgttggac ctctaatgat gggcagttta agcttttgca ggcagaagag    120
gtggctcgtc tctgggggat cgcaagaac aagcctaaca tgaattatga caaactcagc    180
cgagccctca gatactatta tgtaaagaat atcatcaaaa agtgaatgg tcagaagttt    240 gtgtacaagt ttgtctctta tccagagatt ttgaacatgg atccaatgac agtgggcagg    300
attgagggtg actgtgaaag tttaaacttc agtgaagtca gcagcagttc caaagatgtg    360
```

-continued

```
gagaatggag ggaaagataa accacctcag cctggtgcca agacctctag ccgcaatgac      420
tacatacact ctggcttata ttcttcattt actctcaact ctttgaactc ctccaatgta      480
aagcttttca aattgataaa gactgagaat ccagccgaga aactggcaga gaaaaaatct      540
cctcaggagc ccacaccatc tgtcatcaaa tttgtcacga caccttccaa aaagccaccg      600
gttgaacctg ttgctgccac catttcaatt ggcccaagta tttctccatc ttcagaagaa      660
actatccaag ctttggagac attggtttcc ccaaaactgc cttccctgga agccccaacc      720
tctgcctcta acgtaatgac tgcttttgcc accacaccac ccatttcgtc catacccccct    780 ttgcaggaac ctcccagaac accttcacca ccactgagtt ctcacccaga catcgacaca      840
gacattgatt cagtggcttc tcagccaatg gaactttccag agaatttgtc actggagcct    900
aaagaccagg attcagtctt gctagaaaag gacaaagtaa ataattcatc aagatccaag      960
aaacccaaag ggttagaact ggcacccacc cttgtgatca cgagcagtga tccaagccca     1020
ctgggaatac tgagcccatc tctccctaca gcttctctta ccagcatt ttttttcacag       1080 gtagcttgct cgctctttat ggtgtcacca ttgctttcat ttatttgccc ttttaagcaa     1140
atccagaatt tatacactca gtttgctttt ctgttactta ggtttgtctt agaaaggtta     1200
tgtgtgactg tcatgtga                                                   1218

<210> SEQ ID NO 4
<211> LENGTH: 1122
<212> TYPE: DNA
<213> ORGANISM: Artificial Sequence
<220> FEATURE:
<223> OTHER INFORMATION: mouse MesP1 gene sequence

<400> SEQUENCE: 4
gatatcgaat tctggaaggg gcccgcttca cacctagggc tcaggataaa gctacagcgg       60
acccaatggt caggcctccg ttgccatggc ccagcccctg tgcgagccgc gctccgagtc      120
ctggatcctg agtcccgctg gtcggcagcc accgatgcct tccgatggga acagcgtctg      180
ctccccagcc tggtcctcgg acccgtggga cggtgcccag gccagcagcc ctgcaccacc      240
ctgcgcccgc ccggcccggc gtgctgggac cccgggtagg cgcgggacgc acggtagccg      300
cctgggtagc ggacagcggc agagcgccag cgagcgggag aagctacgta tgcgcacact      360
cgcccgcgcg ctgcacgagc tgcgccgctt cttgccgcca tccgtggcac caaccggcca      420
gaacctgacc aagatcgaga cgctgcgcct ggccatccgc tacattggcc acctgtcggc      480
tgtgctggga ctcagcgagg acaacctccg gcgacagcgg cacgcggtgt cacctcgagg      540
ctgcccgctg tgccccgaca gcgacctggc gcagtcgcag tcactcggtc ctggtttaag      600
cccggccgtc tgcagcgggg tgtcgtgggg atccccgcct gcctacccta gaccccgagt      660
cgccgcagaa tcgtgggacc catcgttcca gtacgcagaa acagcatccc aggaaaggca      720
ggaaatggag cccagtccct catctccgct cttcagcagc gacatgctgg ctcttctaga      780 aacctgacg ccgccgcagg agtggccgcc tgcctgaaga gtggagggga caatgcaacg      840
gatgattgtc accctgtctg agcacagaca cttttccttt ggtcttggca ccttcggagg      900
gagtagatcc tggaagaggc ggcagtgata ccaacatggg catcccgggg tgggagctgg      960
ccctcatcca gactgtacca ttccaaccct ccttggaagg aggcgccaa tagggtacac      1020 gctctaaaga tgaagcaggc acaagctttg cctggtgtgt atttatttat ttgtgaataa     1080
accgattgtg ctagtgtcaa aacctggata gtcgatccac ta                        1122
```

<210> SEQ ID NO 5
<211> LENGTH: 243
<212> TYPE: PRT
<213> ORGANISM: Artificial Sequence
<220> FEATURE:
<223> OTHER INFORMATION: mouse MesP1 protein sequence

<400> SEQUENCE: 5

```
Met Ala Gln Pro Leu Cys Glu Pro Arg Ser Glu Ser Trp Ile Leu Ser
1               5                   10                  15

Pro Ala Gly Arg Gln Pro Pro Met Pro Ser Asp Gly Asn Ser Val Cys
            20                  25                  30

Ser Pro Ala Trp Ser Ser Asp Pro Trp Asp Gly Ala Gln Ala Ser Ser
        35                  40                  45

Pro Ala Pro Pro Cys Ala Arg Pro Ala Arg Arg Ala Gly Thr Pro Gly
    50                  55                  60

Arg Arg Gly Thr His Gly Ser Arg Leu Gly Ser Gly Gln Arg Gln Ser
65                  70                  75                  80

Ala Ser Glu Arg Glu Lys Leu Arg Met Arg Thr Leu Ala Arg Ala Leu
                85                  90                  95

His Glu Leu Arg Arg Phe Leu Pro Pro Ser Val Ala Pro Thr Gly Gln
            100                 105                 110

Asn Leu Thr Lys Ile Glu Thr Leu Arg Leu Ala Ile Arg Tyr Ile Gly
        115                 120                 125

His Leu Ser Ala Val Leu Gly Leu Ser Glu Asp Asn Leu Arg Arg Gln
    130                 135                 140

Arg His Ala Val Ser Pro Arg Gly Cys Pro Leu Cys Pro Asp Ser Asp
145                 150                 155                 160

Leu Ala Gln Ser Gln Ser Leu Gly Pro Gly Leu Ser Pro Ala Val Cys
                165                 170                 175

Ser Gly Val Ser Trp Gly Ser Pro Pro Ala Tyr Pro Arg Pro Arg Val
            180                 185                 190

Ala Ala Glu Ser Trp Asp Pro Ser Phe Gln Tyr Ala Glu Thr Ala Ser
        195                 200                 205

Gln Glu Arg Gln Glu Met Glu Pro Ser Pro Ser Ser Pro Leu Phe Ser
    210                 215                 220

Ser Asp Met Leu Ala Leu Leu Glu Thr Trp Thr Pro Pro Gln Glu Trp
225                 230                 235                 240

Pro Pro Ala
```

<210> SEQ ID NO 6
<211> LENGTH: 732
<212> TYPE: DNA
<213> ORGANISM: Artificial Sequence
<220> FEATURE:
<223> OTHER INFORMATION: mouse MesP1 coding sequence

<400> SEQUENCE: 6

| | | | | | |
|---|---|---|---|---|---|
| atggcccagc | ccctgtgcga | gccgcgctcc | gagtcctgga | tcctgagtcc | cgctggtcgg | 60 |
| cagccaccga | tgccttccga | tgggaacagc | gtctgctccc | cagcctggtc | ctcggacccg | 120 |
| tgggacggtg | cccaggccag | cagccctgca | ccaccctgcg | cccgcccggc | ccggcgtgct | 180 |
| gggaccccgg | gtaggcgcgg | gacgcacggt | agccgcctgg | gtagcggaca | gcggcagagc | 240 |
| gccagcgagc | gggagaagct | acgtatgcgc | acactcgccc | gcgcgctgca | cgagctgcgc | 300 |
| cgcttcttgc | cgccatccgt | ggcaccaacc | ggcagaacc | tgaccaagat | cgagacgctg | 360 |
| cgcctggcca | tccgctacat | tggccacctg | tcggctgtgc | tgggactcag | cgaggacaac | 420 |

-continued

| | |
|---|---:|
| ctccggcgac agcggcacgc ggtgtcacct cgaggctgcc cgctgtgccc cgacagcgac | 480 |
| ctggcgcagt cgcagtcact cggtcctggt ttaagcccgg ccgtctgcag cggggtgtcg | 540 |
| tggggatccc cgcctgccta ccctagaccc cgagtcgccg cagaatcgtg ggacccatcg | 600 |
| ttccagtacg cagaaacagc atcccaggaa aggcaggaaa tggagcccag tccctcatct | 660 |
| ccgctcttca gcagcgacat gctggctctt ctagaaacct ggacgccgcc gcaggagtgg | 720 |
| ccgcctgcct ga | 732 |

<210> SEQ ID NO 7
<211> LENGTH: 2500
<212> TYPE: DNA
<213> ORGANISM: Artificial Sequence
<220> FEATURE:
<223> OTHER INFORMATION: human ETS2 gene sequence

<400> SEQUENCE: 7

| | |
|---|---:|
| gtgtcgctcc agctcagagc tcccggagcc gcccggccag cgtccggcct ccctgatcgt | 60 |
| ctctggccgg cgccctcgcc ctcgcccggc gcgcaccgag cagccgcggg cgccgagcag | 120 |
| ccaccgtccc gaccaagcgc cggccctgcc cgcagcggca ggatgaatga tttcggaatc | 180 |
| aagaatatgg accaggtagc ccctgtggct aacagttaca gagggacact caagcgccag | 240 |
| ccagcctttg acacctttga tgggtccctg tttgctgttt ttccttctct aaatgaagag | 300 |
| caaacactgc aagaagtgcc aacaggcttg gattccattt ctcatgactc cgccaactgt | 360 |
| gaattgcctt tgttaacccc gtgcagcaag gctgtgatga gtcaagcctt aaaagctacc | 420 |
| ttcagtggct tcaaaaagga acagcggcgc ctgggcattc aaagaaccc ctggctgtgg | 480 |
| agtgagcaac aggtatgcca gtggcttctc tgggccacca atgagttcag tctggtgaac | 540 |
| gtgaatctgc agaggttcgg catgaatggc cagatgctgt gtaaccttgg caaggaacgc | 600 |
| tttctggagc tggcacctga cttgtgggt gacattctct gggaacatct ggagcaaatg | 660 |
| atcaaagaaa accaagaaaa gacagaagat caatatgaag aaaattcaca cctcacctcc | 720 |
| gttcctcatt ggattaacag caatacatta ggttttggca cagagcaggc gccctatgga | 780 |
| atgcagacac agaattaccc caaaggcggc ctcctggaca gcatgtgtcc ggcctccaca | 840 |
| cccagcgtac tcagctctga gcaggagttt cagatgttcc ccaagtctcg gctcagctcc | 900 |
| gtcagcgtca cctactgctc tgtcagtcag gacttcccag cagcaacctt gaatttgctc | 960 |
| accaacaatt ctgggacgcc caaagaccac gactcccctg agaacggtgc ggacagcttc | 1020 |
| gagagctcag actccctcct ccagtcctgg aacagccagt cgtccttgct ggatgtgcaa | 1080 |
| cgggttcctt ccttcgagag cttcgaagat gactgcagcc agtctctctg cctcaataag | 1140 |
| ccaaccatgt ctttcaagga ttacatccaa gagaggagtg accggtgga gcaaggcaaa | 1200 |
| ccagttatac ctgcagctgt gctggccggc ttcacaggaa gtggacctat tcagctgtgg | 1260 |
| cagtttctcc tggagctgct atcagacaaa tcctgccagt cattcatcag ctggactgga | 1320 |
| gacggatggg agtttaagct cgccgacccc gatgaggtgg cccgccggtg gggaaagagg | 1380 |
| aaaaataagc ccaagatgaa ctacgagaag ctgagccggg gcttacgcta ctattacgac | 1440 |
| aagaacatca tccacaagac gtcggggaag cgctacgtgt accgcttcgt gtgcgacctc | 1500 |
| cagaacttgc tggggttcac gcccgaggaa ctgcacgcca tcctgggcgt ccagcccgac | 1560 |
| acggaggact gaggtcgccg ggaccaccct gagccggccc caggctcgtg gactgagtgg | 1620 |
| gaagcccatc ctgaccagct gctccgagga cccaggaaag gcaggattga aaatgtccag | 1680 |
| gaaagtggcc aagaagcagt ggccttattg catcccaaac cacgcctctt gaccaggctg | 1740 |

```
cctcccttgt ggcagcaacg gcacagctaa ttctactcac agtgctttta agtgaaaatg   1800
gtcgagaaag aggcaccagg aagccgtcct ggcgcctggc agtccgtggg acgggatggt   1860
tctggctgtt tgagattctc aaaggagcga gcatgtcgtg acacacaca gactattttt    1920 agattttctt ttgccttttg caaccaggaa cagcaaatgc aaaaactctt tgagagggta   1980
ggagggtggg aaggaaacaa ccatgtcatt tcagaagtta gtttgtatat attattataa   2040
tcttataatt gttctcagaa tcccttaaca gttgtattta acagaaattg tatattgtaa   2100
tttaaaataa ttatataact gtatttgaaa taagaattca gacatctgag gttttatttc   2160 attttcaat agcacatatg gaattttgca aagatttaat ctgccaaggg ccgactaaga    2220
gaagttgtaa agtatgtatt atttacattt aatagactta cagggataag gcctgtgggg   2280
ggtaatccct gcttttgtg tttttttgtt tgtttgtttg tttgttttg ggggttttc     2340 ttgccttggt tgtctggcaa ggactttgta catttgggag tttttatgag aaacttaaat   2400
gttattatct gggcttatat ctggcctctg ctttctcctt taattgtaaa gtaaagcta   2460 taaagcagta tttttcttga caaaaaaaaa aaaaaaaaa                          2500
```

<210> SEQ ID NO 8
<211> LENGTH: 469
<212> TYPE: PRT
<213> ORGANISM: Artificial Sequence
<220> FEATURE:
<223> OTHER INFORMATION: human ETS2 protein sequence

<400> SEQUENCE: 8

```
Met Asn Asp Phe Gly Ile Lys Asn Met Asp Gln Val Ala Pro Val Ala
1               5                   10                  15

Asn Ser Tyr Arg Gly Thr Leu Lys Arg Gln Pro Ala Phe Asp Thr Phe
            20                  25                  30

Asp Gly Ser Leu Phe Ala Val Phe Pro Ser Leu Asn Glu Glu Gln Thr
        35                  40                  45

Leu Gln Glu Val Pro Thr Gly Leu Asp Ser Ile Ser His Asp Ser Ala
    50                  55                  60

Asn Cys Glu Leu Pro Leu Leu Thr Pro Cys Ser Lys Ala Val Met Ser
65                  70                  75                  80

Gln Ala Leu Lys Ala Thr Phe Ser Gly Phe Lys Lys Glu Gln Arg Arg
                85                  90                  95

Leu Gly Ile Pro Lys Asn Pro Trp Leu Trp Ser Glu Gln Gln Val Cys
            100                 105                 110

Gln Trp Leu Leu Trp Ala Thr Asn Glu Phe Ser Leu Val Asn Val Asn
        115                 120                 125

Leu Gln Arg Phe Gly Met Asn Gly Gln Met Leu Cys Asn Leu Gly Lys
    130                 135                 140

Glu Arg Phe Leu Glu Leu Ala Pro Asp Phe Val Gly Asp Ile Leu Trp
145                 150                 155                 160

Glu His Leu Glu Gln Met Ile Lys Glu Asn Gln Glu Lys Thr Glu Asp
                165                 170                 175

Gln Tyr Glu Glu Asn Ser His Leu Thr Ser Val Pro His Trp Ile Asn
            180                 185                 190

Ser Asn Thr Leu Gly Phe Gly Thr Glu Gln Ala Pro Tyr Gly Met Gln
        195                 200                 205

Thr Gln Asn Tyr Pro Lys Gly Gly Leu Leu Asp Ser Met Cys Pro Ala
    210                 215                 220

Ser Thr Pro Ser Val Leu Ser Ser Glu Gln Glu Phe Gln Met Phe Pro
225                 230                 235                 240
```

```
Lys Ser Arg Leu Ser Ser Val Ser Val Thr Tyr Cys Ser Val Ser Gln
                245                 250                 255
Asp Phe Pro Gly Ser Asn Leu Asn Leu Leu Thr Asn Asn Ser Gly Thr
            260                 265                 270
Pro Lys Asp His Asp Ser Pro Glu Asn Gly Ala Asp Ser Phe Glu Ser
        275                 280                 285
Ser Asp Ser Leu Leu Gln Ser Trp Asn Ser Gln Ser Ser Leu Leu Asp
    290                 295                 300
Val Gln Arg Val Pro Ser Phe Glu Ser Phe Glu Asp Cys Ser Gln
305                 310                 315                 320
Ser Leu Cys Leu Asn Lys Pro Thr Met Ser Phe Lys Asp Tyr Ile Gln
                325                 330                 335
Glu Arg Ser Asp Pro Val Glu Gln Gly Lys Pro Val Ile Pro Ala Ala
            340                 345                 350
Val Leu Ala Gly Phe Thr Gly Ser Gly Pro Ile Gln Leu Trp Gln Phe
        355                 360                 365
Leu Leu Glu Leu Leu Ser Asp Lys Ser Cys Gln Ser Phe Ile Ser Trp
    370                 375                 380
Thr Gly Asp Gly Trp Glu Phe Lys Leu Ala Asp Pro Asp Glu Val Ala
385                 390                 395                 400
Arg Arg Trp Gly Lys Arg Lys Asn Lys Pro Lys Met Asn Tyr Glu Lys
                405                 410                 415
Leu Ser Arg Gly Leu Arg Tyr Tyr Tyr Asp Lys Asn Ile Ile His Lys
            420                 425                 430
Thr Ser Gly Lys Arg Tyr Val Tyr Arg Phe Val Cys Asp Leu Gln Asn
        435                 440                 445
Leu Leu Gly Phe Thr Pro Glu Glu Leu His Ala Ile Leu Gly Val Gln
    450                 455                 460
Pro Asp Thr Glu Asp
465

<210> SEQ ID NO 9
<211> LENGTH: 1410
<212> TYPE: DNA
<213> ORGANISM: Artificial Sequence
<220> FEATURE:
<223> OTHER INFORMATION: human ETS2 coding sequence

<400> SEQUENCE: 9
atgaatgatt tcggaatcaa gaatatggac caggtagccc tgtggctaa cagttacaga      60 gggacactca agcgccagcc agcctttgac acctttgatg ggtccctgtt tgctgttttt     120
ccttctctaa atgaagagca acactgcaa gaagtgccaa caggcttgga ttccatttct     180
catgactccg ccaactgtga attgcctttg ttaaccccgt gcagcaaggc tgtgatgagt     240
caagccttaa aagctacctt cagtggcttc aaaaaggaac agcggcgcct gggcattcca     300
aagaacccct ggctgtggag tgagcaacag gtatgccagt ggcttctctg gccaccaat     360 gagttcagtc tggtgaacgt gaatctgcag aggttcggca tgaatggcca gatgctgtgt     420
aaccttggca aggaacgctt tctggagctg gcacctgact ttgtgggtga cattctctgg     480
gaacatctgg agcaaatgat caagaaaac caagaaaaga cagaagatca atatgaagaa     540
aattcacacc tcacctccgt tcctcattgg attaacagca atacattagg ttttggcaca     600
gagcaggcgc cctatggaat gcagacacag aattacccca aaggcggcct cctggacagc     660
atgtgtccgg cctccacacc cagcgtactc agctctgagc aggagtttca gatgttcccc     720
```

| | |
|---|---|
| aagtctcggc tcagctccgt cagcgtcacc tactgctctg tcagtcagga cttcccaggc | 780 |
| agcaacttga atttgctcac caacaattct gggacgccca agaccacga ctcccctgag | 840 |
| aacggtgcgg acagcttcga gagctcagac tccctcctcc agtcctggaa cagccagtcg | 900 |
| tccttgctgg atgtgcaacg ggttccttcc ttcgagagct tcgaagatga ctgcagccag | 960 |
| tctctctgcc tcaataagcc aaccatgtct ttcaaggatt acatccaaga gaggagtgac | 1020 |
| ccggtgggag aaggcaaacc agttatacct gcagctgtgc tggccggctt cacaggaagt | 1080 |
| ggacctattc agctgtggca gtttctcctg gagctgctat cagacaaatc ctgccagtca | 1140 |
| ttcatcagct ggactggaga cggatgggag tttaagctcg ccgacccga tgaggtggcc | 1200 |
| cgccggtggg gaaagaggaa aaataagccc aagatgaact acgagaagct gagccggggc | 1260 |
| ttacgctact attacgacaa gaacatcatc cacaagacgt cggggaagcg ctacgtgtac | 1320 |
| cgcttcgtgt gcgacctcca gaacttgctg gggttcacgc ccgaggaact gcacgccatc | 1380 |
| ctgggcgtcc agcccgacac ggaggactga | 1410 |

<210> SEQ ID NO 10
<211> LENGTH: 5143
<212> TYPE: DNA
<213> ORGANISM: Artificial Sequence
<220> FEATURE:
<223> OTHER INFORMATION: human ETS sequence

<400> SEQUENCE: 10

| | |
|---|---|
| agttggaaag agaccacaga ctttgaggga agctcactca ggatctgctc tccggcaaag | 60 |
| tagtaagtga ggtgctgaga gcagaatgag ctactttgtg gattctgctg ggagcagccc | 120 |
| cgtcccttac tcagcgcctc gtcctgcagt ggtgaggcaa ggacctagca acacttatga | 180 |
| agatcctcga atgaactgtg gtttccagtc caattatcac cagcaaagac cttgctaccc | 240 |
| cttttgggat gagatggcaa ctcaggaagt tcctactggt cttgaacact gtgtctcaga | 300 |
| tatggaatgt gcagatgtcc cactattaac tccaagcagc aaagaaatga tgtctcaagc | 360 |
| attaaaagct actttcagtg gtttcactaa agaacagcaa cgactgggga tcccaaaaga | 420 |
| cccccggcag tggacagaaa cccatgttcg ggactgggtg atgtgggctg tgaatgaatt | 480 |
| cagcctgaaa ggtgtagact tccagaagtt ctgtatgaat ggagcagccc tctgcgccct | 540 |
| gggtaaagac tgctttctcg agctggcccc agactttgtt ggggacatct tatgggaaca | 600 |
| tctagagatc ctgcagaaag aggatgtgaa accatatcaa gttaatggag tcaacccagc | 660 |
| ctatccagaa tcccgctata cctcggatta cttcattagc tatggtattg agcatgccca | 720 |
| gtgtgttcca ccatcggagt tctcagagcc cagcttcatc acagagtcct atcagacgct | 780 |
| ccatcccatc agctcggaag agctcctctc cctcaagtat gagaatgact ccccctcggt | 840 |
| cattctccga gaccctctcc agacagacac cttgcagaat gactactttg ctatcaaaca | 900 |
| agaagtcgtc accccagaca catgtgcat ggggaggacc agtcgtggta aactcggggg | 960 |
| ccaggactct tttgaaagca tagagagcta cgatagttgt gatcgcctca cccagtcctg | 1020 |
| gagcagccag tcatctttca acagcctgca gcgtgttccc tcctatgaca gcttcgactc | 1080 |
| agaggactat ccggctgccc tgcccaacca caagcccaag gcaccttca aggactatgt | 1140 |
| gcgggaccgt gctgacctca ataaggacaa gcctgtcatt cctgctgctg ccctagctgg | 1200 |
| ctacacaggc agtggaccaa tccagctatg gcagtttctt ctggaattac tcactgataa | 1260 |
| atcctgtcag tcttttatca gctggacagg agatggctgg gaattcaaac tttctgaccc | 1320 |
| agatgaggtg gccaggagat ggggaaagag gaaaaacaaa cctaagatga attatgagaa | 1380 |

```
actgagccgt ggcctacgct actattacga caaaaacatc atccacaaga cagcggggaa    1440
acgctacgtg taccgctttg tgtgtgacct gcagagcctg ctggggtaca cccctgagga    1500
gctgcacgcc atgctggacg tcaagccaga tgccgacgag tgatggcact gaaggggctg    1560
gggaaaccct gctgagacct tccaaggaca gccgtgttgg ttggactctg aattttgaat    1620
tgttattcta ttttttattt tccagaactc attttttacc ttcaggggtg ggagctaagt    1680
cagttgcagc tgtaatcaat tgtgcgcagt tgggaaagga aagccaggac ttgtggggtg    1740
ggtgggacca gaaattcttg agcaaatttt caggagaggg agaagggcct tctcagaagc    1800
ttgaaggctc tggcttaaca gagaaagaga ctaatgtgtc caatcatttt taaaaatcat    1860
ccatgaaaaa gtgtcttgag ttgtggaccc attagcaagt gacattgtca catcagaact    1920
catgaaactg atgtaaggca attaatttgc ttctgttttt aggtctggga gggcaaaaaa    1980
gaggtgggtg ggatgaaaca tgttttgggg ggggatgcac tgaaaatctg agaactattt    2040
acctatcact ctagttttga agcaaagatg gacttcagtg gggaggggcc aaaaccgttg    2100
ttgtgttaaa atttatttta ttaaattttg tgccagtatt tttttttctta aaaatcgtct    2160 taagctctaa ggtggtctca gtattgcaat atcatgtaag tttgttttta tttgccggct    2220
gaggattctg tcacaatgaa agaaaactgt ttatatagac cccattggaa aagcaaaacg    2280
ctctcactga gatcagggat cccaaaattca tgggacttat ataagaagga caattaatgc    2340
tgatttgggt acaggggaat tatgtgtgtg aatgtcatct acaattaaaa aaaattagca    2400 catccctta cttacttgtt atcagtggat tctcggggtt tggacttaat gttgagctaa    2460
gaagcattaa gtctttgaac tgaatgtatt ttgcatccct ggttttggac gacagtaaac    2520
gtaggagcac tgttgaagtc ctggaaggga gatcgaagga ggaagattga cttggttctt    2580
tcttagtcct atatctgtag catagatgac ttggaataaa agctgtatgc atgggcatta    2640
cccctcaggt cctaagaaat aagtcctgaa tgcatgtcgt tccaaactaa cactctgtaa    2700 ttttttctttt atgtcttatt ttccaagagt cctccatttt ttgcaccccc tcaccgccaa    2760
ctctgttatt cagtagagag aagtgtacgg cttttctgatt ggtgagtgaa aaagtaactt    2820
gagacacgac ctaagttgaa gagtttagac ttgctgagtt ttagaagtga tggaaattaa    2880
gagagcattt caataaaatg tgacttggct gtctttggaa gagaagtgca aggctttcct    2940
ttgaagaatt taaattagtc cggtaggatg tcaggtgaga ctgtgtatgc aaaatgaatg    3000
gcacaggtga tgccagggcc tcttgcttgg gtctgatgtc ttggcacagg gtaagtgaag    3060
gttaattcca gaagagagga atgacttgaa ggcaaaggaa actaaggaag gaggttcagt    3120
gaggaaaata aggttgtcca tgagatttga atagattttt agttccccca aggtttaaat    3180
acaaacatag tcaagcaagg tagtcatctt tctgctggtt gtgaggggga atctgaaaat    3240
ggagttttag aggaaaagtc aacatctaac tagtgaggaa aagtgcctaa tacaattaga    3300
atctccctca ctctatagtt gcccagttga aaggataagg aggaggggtg gcttttatgg    3360
acttccatga gagaaggaaa gaaatatttc aggtaagctt ctcagggctg gccccttttg    3420
ggatttggat gagaaattgg aagtactaac tactttctag catatcttta agaaaattga    3480 ttgttatttta ctcccagatc ctcttgcaga cccagaatta tcaggaacat agctctgtga    3540
ttcatgagtc tccccatact gatgaattgg agcatccata tggaaagcaa aggcagaatt    3600
atcccagctg tattattttg atcttttgga tgcaggtgcc ttaatgaagc tctcaaaata    3660
ttttaggagc tgctcaggga gtgttgggtg gaactgtttg gactacattg ttttctctta    3720
gattatgtga ttttgttgg gcactggcaa aaggtgtgtg tgtgaatgtg tgcatgtgtg    3780
```

```
tgaatgttgt gtgtgtgtgt gtgtgtgtgt gtgtgtgtgt gtttgcagac      3840
atgcaaaact gcagctgaaa taataccctta gatttctagg taagtctttc cacatttcaa   3900
taatgggtaa gagtagaacc agggccgggt atcaattatt gcttgctgtt tgcaaccagg   3960
cataaaatca ctttctcaaa tcatccaccg ttcctattaa atttatgccg gaaactctcc   4020
ttctgtgagt ataactcctg cagttcctat agcagataag atataagaaa gtgcctccta   4080
gtgctcctcc gcccgcttgt ttgctaaaat tcccttctc tctaagtcca ccattttcaa    4140
gatttgtaga tagtgtatta gttaagacag ctttgtcgat ctggccagat gttttttctc   4200
ctttgtccaa aggccagaga ccatcccagg aagagtggtg ggtggtttat acactggaaa   4260
tgttgcgttt atgcttttta aaaacacacg ttaacttcag aggaaggatg ggcaaatctg   4320
gtctagctgg gtgaaaccct tattttccca gagatgcctt aacctttgtt ggttttggct   4380
ttagggttca gagtcacttt tgttcccttc tccattctgg agagggactt cccctacata   4440
gagccctgat ttttgtggct gtggggattg gaggtagcat tcaaagatca gatgtgcttt   4500
tcctcacttt ggagatgaac actctgggtt ttacagcatt aacctgccta accttcatgg   4560
tgagaaatac accatctctc ttctagtcat gctgtgcatg ccgcttactc tgttggggtc   4620
tatataaatt tgttgaactc ttacctacat tccaaagaag tttcaaggaa ccataaatat   4680
atgtatacat atacatatat aaaatatata tattaaaata aaattatcag gaatactgcc   4740
tcagttattg aactttttt tttaagaata cttttttttt aagctgagaa gtatagggat    4800
gaaaaagatg ttatattgtg tttgactatt ttccaacttg tattttcata taatttatat   4860
tttttaaaag ctgaaaattt agaagcaaga tgaaaaaaag gaaaagcagg tgcttttaa    4920 aaatcagaac tgaggtagct tagagatgta gcgatgtaag tgtcgatgtt ttttaaaaa    4980 aaaatgcaaa aaaattctta tggcggagtt ttttgtttgt ttattttagt agctgatgct   5040
ggcacatcat tttgctggag agttttttat atactgtagc ctgatttcat attgtatttt   5100
aaactgtgtg aaattaaaaa caaagaattt cattcataat gct                    5143
```

<210> SEQ ID NO 11
<211> LENGTH: 21
<212> TYPE: DNA
<213> ORGANISM: Artificial Sequence
<220> FEATURE:
<223> OTHER INFORMATION: GapdhFP crtl exp primer

<400> SEQUENCE: 11
tgttgccatc aatgacccct t                                             21

<210> SEQ ID NO 12
<211> LENGTH: 19
<212> TYPE: DNA
<213> ORGANISM: Artificial Sequence
<220> FEATURE:
<223> OTHER INFORMATION: GapdhRP ctrl exp primer

<400> SEQUENCE: 12
ctccacgacg tactcagcg                                                19

<210> SEQ ID NO 13
<211> LENGTH: 20
<212> TYPE: DNA
<213> ORGANISM: Artificial Sequence
<220> FEATURE:
<223> OTHER INFORMATION: hNanogFP ctrl exp primer

<400> SEQUENCE: 13

```
cagaaggcct cagcacctac                                              20

<210> SEQ ID NO 14
<211> LENGTH: 22
<212> TYPE: DNA
<213> ORGANISM: Artificial Sequence
<220> FEATURE:
<223> OTHER INFORMATION: hNanogRP ctrl exp primer

<400> SEQUENCE: 14
tatagaaggg actgttccag gc                                           22

<210> SEQ ID NO 15
<211> LENGTH: 22
<212> TYPE: DNA
<213> ORGANISM: Artificial Sequence
<220> FEATURE:
<223> OTHER INFORMATION: hOct 3/4FP ctrl exp primer

<400> SEQUENCE: 15
cttgaatccc gaatggaaag gg                                           22

<210> SEQ ID NO 16
<211> LENGTH: 21
<212> TYPE: DNA
<213> ORGANISM: Artificial Sequence
<220> FEATURE:
<223> OTHER INFORMATION: hOct 3/4 RP ctrl exp primer

<400> SEQUENCE: 16
ccttcccaaa tagaaccccc a                                            21

<210> SEQ ID NO 17
<211> LENGTH: 19
<212> TYPE: DNA
<213> ORGANISM: Artificial Sequence
<220> FEATURE:
<223> OTHER INFORMATION: Sox2 HPB F primer

<400> SEQUENCE: 17
tggacagtta cgcgcacat                                               19

<210> SEQ ID NO 18
<211> LENGTH: 21
<212> TYPE: DNA
<213> ORGANISM: Artificial Sequence
<220> FEATURE:
<223> OTHER INFORMATION: Sox2 HPB R primer

<400> SEQUENCE: 18
cgagtaggac atgctgtagg t                                            21

<210> SEQ ID NO 19
<211> LENGTH: 22
<212> TYPE: DNA
<213> ORGANISM: Artificial Sequence
<220> FEATURE:
<223> OTHER INFORMATION: hRex1FP ctrl exp primer

<400> SEQUENCE: 19
gctgaccacc agcacactag gc                                           22

<210> SEQ ID NO 20
<211> LENGTH: 24
<212> TYPE: DNA
<213> ORGANISM: Artificial Sequence
<220> FEATURE:
```

```
<223> OTHER INFORMATION: hRex1RPctrl exp primer

<400> SEQUENCE: 20
tttctggtgt cttgtctttg cccg                                          24

<210> SEQ ID NO 21
<211> LENGTH: 20
<212> TYPE: DNA
<213> ORGANISM: Artificial Sequence
<220> FEATURE:
<223> OTHER INFORMATION: c-Myc HPB F primer

<400> SEQUENCE: 21
aggcgaacac acaacgtctt                                               20

<210> SEQ ID NO 22
<211> LENGTH: 21
<212> TYPE: DNA
<213> ORGANISM: Artificial Sequence
<220> FEATURE:
<223> OTHER INFORMATION: c-Myc HPB R primer

<400> SEQUENCE: 22
ttggacggac aggatgtatg c                                             21

<210> SEQ ID NO 23
<211> LENGTH: 24
<212> TYPE: DNA
<213> ORGANISM: Artificial Sequence
<220> FEATURE:
<223> OTHER INFORMATION: hKlf4FP ctrl exp primer

<400> SEQUENCE: 23
atggctgtca gcgacgcgct gctc                                          24

<210> SEQ ID NO 24
<211> LENGTH: 24
<212> TYPE: DNA
<213> ORGANISM: Artificial Sequence
<220> FEATURE:
<223> OTHER INFORMATION: hKlf4RP ctrl exp primer

<400> SEQUENCE: 24
cgttgaactc ctcggtctct ctcc                                          24

<210> SEQ ID NO 25
<211> LENGTH: 22
<212> TYPE: DNA
<213> ORGANISM: Artificial Sequence
<220> FEATURE:
<223> OTHER INFORMATION: Nkx 2.5 FP primer

<400> SEQUENCE: 25
ccctgaccga tcccacctca ac                                            22

<210> SEQ ID NO 26
<211> LENGTH: 21
<212> TYPE: DNA
<213> ORGANISM: Artificial Sequence
<220> FEATURE:
<223> OTHER INFORMATION: Nkx 2.5 RP primer

<400> SEQUENCE: 26
ggcgggcgac ggcgagatag c                                             21

<210> SEQ ID NO 27
```

-continued

```
<211> LENGTH: 22
<212> TYPE: DNA
<213> ORGANISM: Artificial Sequence
<220> FEATURE:
<223> OTHER INFORMATION: Mesp 1 FP primer

<400> SEQUENCE: 27
tcgaagtggt tccttggcag ac                                              22

<210> SEQ ID NO 28
<211> LENGTH: 23
<212> TYPE: DNA
<213> ORGANISM: Artificial Sequence
<220> FEATURE:
<223> OTHER INFORMATION: Mesp 1 RP primer

<400> SEQUENCE: 28
cctcctgctt gcctcaaagt gtc                                             23

<210> SEQ ID NO 29
<211> LENGTH: 25
<212> TYPE: DNA
<213> ORGANISM: Artificial Sequence
<220> FEATURE:
<223> OTHER INFORMATION: Mesp 2 FP primer

<400> SEQUENCE: 29
cgctgcgcct ggccatccgc tacat                                           25

<210> SEQ ID NO 30
<211> LENGTH: 21
<212> TYPE: DNA
<213> ORGANISM: Artificial Sequence
<220> FEATURE:
<223> OTHER INFORMATION: Mesp 2 RP primer

<400> SEQUENCE: 30
gccccaaggg gaccccgcga c                                               21

<210> SEQ ID NO 31
<211> LENGTH: 20
<212> TYPE: DNA
<213> ORGANISM: Artificial Sequence
<220> FEATURE:
<223> OTHER INFORMATION: Mef2c FP primer

<400> SEQUENCE: 31
gcaccagtgc agggaacggg                                                 20

<210> SEQ ID NO 32
<211> LENGTH: 21
<212> TYPE: DNA
<213> ORGANISM: Artificial Sequence
<220> FEATURE:
<223> OTHER INFORMATION: Mef2c RP primer

<400> SEQUENCE: 32
gactgagccg actgggagtt a                                               21

<210> SEQ ID NO 33
<211> LENGTH: 19
<212> TYPE: DNA
<213> ORGANISM: Artificial Sequence
<220> FEATURE:
<223> OTHER INFORMATION: Sox 17 FP primer

<400> SEQUENCE: 33
```

```
gcggcgcaag caggtgaag                                                    19

<210> SEQ ID NO 34
<211> LENGTH: 23
<212> TYPE: DNA
<213> ORGANISM: Artificial Sequence
<220> FEATURE:
<223> OTHER INFORMATION: ACTCTGGCAGTCGCGGTAGTGGC

<400> SEQUENCE: 34
actctggcag tcgcggtagt ggc                                               23

<210> SEQ ID NO 35
<211> LENGTH: 23
<212> TYPE: DNA
<213> ORGANISM: Artificial Sequence
<220> FEATURE:
<223> OTHER INFORMATION: FoxA2 FP primer

<400> SEQUENCE: 35
ctgaagccgg aacaccacta cgc                                               23

<210> SEQ ID NO 36
<211> LENGTH: 23
<212> TYPE: DNA
<213> ORGANISM: Artificial Sequence
<220> FEATURE:
<223> OTHER INFORMATION: FoxA2 RP primer

<400> SEQUENCE: 36
tccaggcccg ttttgttcgt gac                                               23

<210> SEQ ID NO 37
<211> LENGTH: 22
<212> TYPE: DNA
<213> ORGANISM: Artificial Sequence
<220> FEATURE:
<223> OTHER INFORMATION: FGF8 FP primer

<400> SEQUENCE: 37
agctcagccg ccgcctcatc cg                                                22

<210> SEQ ID NO 38
<211> LENGTH: 23
<212> TYPE: DNA
<213> ORGANISM: Artificial Sequence
<220> FEATURE:
<223> OTHER INFORMATION: FGF8 RP primer

<400> SEQUENCE: 38
agccctcgta cttggcattc tgc                                               23

<210> SEQ ID NO 39
<211> LENGTH: 23
<212> TYPE: DNA
<213> ORGANISM: Artificial Sequence
<220> FEATURE:
<223> OTHER INFORMATION: MyoD FP primer

<400> SEQUENCE: 39
aggggctagg ttcagctttc tcg                                               23

<210> SEQ ID NO 40
<211> LENGTH: 23
<212> TYPE: DNA
<213> ORGANISM: Artificial Sequence
<220> FEATURE:
```

<223> OTHER INFORMATION: MyoD RP primer

<400> SEQUENCE: 40
ctcctgctct ggcaaagcaa ctc                                            23

<210> SEQ ID NO 41
<211> LENGTH: 21
<212> TYPE: DNA
<213> ORGANISM: Artificial Sequence
<220> FEATURE:
<223> OTHER INFORMATION: BMP2 HBP FP primer

<400> SEQUENCE: 41
acctttatgg agggaaaccc a                                              21

<210> SEQ ID NO 42
<211> LENGTH: 21
<212> TYPE: DNA
<213> ORGANISM: Artificial Sequence
<220> FEATURE:
<223> OTHER INFORMATION: BMP2 HBP RP primer

<400> SEQUENCE: 42
ccggatctgg ttcaagcatg a                                              21

<210> SEQ ID NO 43
<211> LENGTH: 20
<212> TYPE: DNA
<213> ORGANISM: Artificial Sequence
<220> FEATURE:
<223> OTHER INFORMATION: hTert HBP FP primer

<400> SEQUENCE: 43
aaccttcctc agctatgccc                                                20

<210> SEQ ID NO 44
<211> LENGTH: 19
<212> TYPE: DNA
<213> ORGANISM: Artificial Sequence
<220> FEATURE:
<223> OTHER INFORMATION: hTert HBP RP primer

<400> SEQUENCE: 44
gcgtgaaacc tgtacgcct                                                 19

<210> SEQ ID NO 45
<211> LENGTH: 20
<212> TYPE: DNA
<213> ORGANISM: Artificial Sequence
<220> FEATURE:
<223> OTHER INFORMATION: Islet-1 HPB F primer

<400> SEQUENCE: 45
gtggagaggg ccagtctagg                                                20

<210> SEQ ID NO 46
<211> LENGTH: 21
<212> TYPE: DNA
<213> ORGANISM: Artificial Sequence
<220> FEATURE:
<223> OTHER INFORMATION: Islet-1 HPB R primer

<400> SEQUENCE: 46
ccgtcatctc taccagttgc t                                              21

<210> SEQ ID NO 47

```
<211> LENGTH: 19
<212> TYPE: DNA
<213> ORGANISM: Artificial Sequence
<220> FEATURE:
<223> OTHER INFORMATION: Troponin T HPB F primer

<400> SEQUENCE: 47
gagttgcagg cgctgattg                                                    19

<210> SEQ ID NO 48
<211> LENGTH: 22
<212> TYPE: DNA
<213> ORGANISM: Artificial Sequence
<220> FEATURE:
<223> OTHER INFORMATION: Troponin T HPB R primer

<400> SEQUENCE: 48
tctggatgta accccaaaa tg                                                 22

<210> SEQ ID NO 49
<211> LENGTH: 23
<212> TYPE: DNA
<213> ORGANISM: Artificial Sequence
<220> FEATURE:
<223> OTHER INFORMATION: Dhand HPB F primer

<400> SEQUENCE: 49
atgagtctgg taggtggttt tcc                                               23

<210> SEQ ID NO 50
<211> LENGTH: 21
<212> TYPE: DNA
<213> ORGANISM: Artificial Sequence
<220> FEATURE:
<223> OTHER INFORMATION: Dhand HPB R primer

<400> SEQUENCE: 50
catactcggg gctgtaggac a                                                 21

<210> SEQ ID NO 51
<211> LENGTH: 21
<212> TYPE: DNA
<213> ORGANISM: Artificial Sequence
<220> FEATURE:
<223> OTHER INFORMATION: T HPB F primer

<400> SEQUENCE: 51
gatcacgcag ctcaagattg c                                                 21

<210> SEQ ID NO 52
<211> LENGTH: 21
<212> TYPE: DNA
<213> ORGANISM: Artificial Sequence
<220> FEATURE:
<223> OTHER INFORMATION: T HPB R primer

<400> SEQUENCE: 52
tctctggtgt gttcctagac g                                                 21

<210> SEQ ID NO 53
<211> LENGTH: 21
<212> TYPE: DNA
<213> ORGANISM: Artificial Sequence
<220> FEATURE:
<223> OTHER INFORMATION: T5 HPB F primer

<400> SEQUENCE: 53
```
cacttctccg ctcacttcac c                                            21

<210> SEQ ID NO 54
<211> LENGTH: 20
<212> TYPE: DNA
<213> ORGANISM: Artificial Sequence
<220> FEATURE:
<223> OTHER INFORMATION: T5 HPB R primer

<400> SEQUENCE: 54
tggcacgcca tgagagtaga                                              20

<210> SEQ ID NO 55
<211> LENGTH: 21
<212> TYPE: DNA
<213> ORGANISM: Artificial Sequence
<220> FEATURE:
<223> OTHER INFORMATION: ETS-2 HPB F primer

<400> SEQUENCE: 55
aaagctacct tcagtggctt c                                            21

<210> SEQ ID NO 56
<211> LENGTH: 21
<212> TYPE: DNA
<213> ORGANISM: Artificial Sequence
<220> FEATURE:
<223> OTHER INFORMATION: ETS-2 HPB R primer

<400> SEQUENCE: 56
aatgtcaccc acaaagtcag g                                            21

<210> SEQ ID NO 57
<211> LENGTH: 21
<212> TYPE: DNA
<213> ORGANISM: Artificial Sequence
<220> FEATURE:
<223> OTHER INFORMATION: Dkk-1 FP primer

<400> SEQUENCE: 57
attccaacgc tatcaagaac c                                            21

<210> SEQ ID NO 58
<211> LENGTH: 22
<212> TYPE: DNA
<213> ORGANISM: Artificial Sequence
<220> FEATURE:
<223> OTHER INFORMATION: Dkk-1 RP primer

<400> SEQUENCE: 58
ccaaggtgct atgatcatta cc                                           22

<210> SEQ ID NO 59
<211> LENGTH: 20
<212> TYPE: DNA
<213> ORGANISM: Artificial Sequence
<220> FEATURE:
<223> OTHER INFORMATION: TBX 20 FP primer

<400> SEQUENCE: 59
tccagattct ccttttaccg                                              20

<210> SEQ ID NO 60
<211> LENGTH: 20
<212> TYPE: DNA
<213> ORGANISM: Artificial Sequence
<220> FEATURE:

<223> OTHER INFORMATION: TBX 20 RP primer

<400> SEQUENCE: 60
ttcagacttc aggttgagca                                                20

<210> SEQ ID NO 61
<211> LENGTH: 20
<212> TYPE: DNA
<213> ORGANISM: Artificial Sequence
<220> FEATURE:
<223> OTHER INFORMATION: SM actin HBP F primer

<400> SEQUENCE: 61
cggtgctgtc tctctatgcc                                                20

<210> SEQ ID NO 62
<211> LENGTH: 21
<212> TYPE: DNA
<213> ORGANISM: Artificial Sequence
<220> FEATURE:
<223> OTHER INFORMATION: SM actin HBP R primer

<400> SEQUENCE: 62
cacgctcagt caggatcttc a                                              21

<210> SEQ ID NO 63
<211> LENGTH: 21
<212> TYPE: DNA
<213> ORGANISM: Artificial Sequence
<220> FEATURE:
<223> OTHER INFORMATION: hGATA1 F primer

<400> SEQUENCE: 63
agaagcgcct gattgtcagt a                                              21

<210> SEQ ID NO 64
<211> LENGTH: 21
<212> TYPE: DNA
<213> ORGANISM: Artificial Sequence
<220> FEATURE:
<223> OTHER INFORMATION: hGATA1 R primer

<400> SEQUENCE: 64
agagacttgg gttgtccaga a                                              21

<210> SEQ ID NO 65
<211> LENGTH: 19
<212> TYPE: DNA
<213> ORGANISM: Artificial Sequence
<220> FEATURE:
<223> OTHER INFORMATION: hGTAT2 F primer

<400> SEQUENCE: 65
ggcccactct ctgtgtacc                                                 19

<210> SEQ ID NO 66
<211> LENGTH: 21
<212> TYPE: DNA
<213> ORGANISM: Artificial Sequence
<220> FEATURE:
<223> OTHER INFORMATION: hGATA2 R primer

<400> SEQUENCE: 66
catcttcatg ctctccgtca g                                              21

<210> SEQ ID NO 67

```
<211> LENGTH: 19
<212> TYPE: DNA
<213> ORGANISM: Artificial Sequence
<220> FEATURE:
<223> OTHER INFORMATION: TBX3-1 F primer

<400> SEQUENCE: 67
gtgtctcggg cctggattc                                                  19

<210> SEQ ID NO 68
<211> LENGTH: 21
<212> TYPE: DNA
<213> ORGANISM: Artificial Sequence
<220> FEATURE:
<223> OTHER INFORMATION: TBX3-1 R primer

<400> SEQUENCE: 68
acgtgtaggg gtaagggaac a                                               21

<210> SEQ ID NO 69
<211> LENGTH: 23
<212> TYPE: DNA
<213> ORGANISM: Artificial Sequence
<220> FEATURE:
<223> OTHER INFORMATION: TBX3-2 F primer

<400> SEQUENCE: 69
ttaaagtgag atgttctggg ctg                                             23

<210> SEQ ID NO 70
<211> LENGTH: 22
<212> TYPE: DNA
<213> ORGANISM: Artificial Sequence
<220> FEATURE:
<223> OTHER INFORMATION: TBX3-2 R primer

<400> SEQUENCE: 70
actataattc ccctgccacg ta                                              22

<210> SEQ ID NO 71
<211> LENGTH: 22
<212> TYPE: DNA
<213> ORGANISM: Artificial Sequence
<220> FEATURE:
<223> OTHER INFORMATION: TBX4 F primer

<400> SEQUENCE: 71
tgaccatcgc tacaagttct gt                                              22

<210> SEQ ID NO 72
<211> LENGTH: 22
<212> TYPE: DNA
<213> ORGANISM: Artificial Sequence
<220> FEATURE:
<223> OTHER INFORMATION: TBX4 R primer

<400> SEQUENCE: 72
ggtggttgtt tgtcagcttc ag                                              22

<210> SEQ ID NO 73
<211> LENGTH: 21
<212> TYPE: DNA
<213> ORGANISM: Artificial Sequence
<220> FEATURE:
<223> OTHER INFORMATION: TBX6 F primer

<400> SEQUENCE: 73
```
acaccccuaa actggattgc t    21

<210> SEQ ID NO 74
<211> LENGTH: 21
<212> TYPE: DNA
<213> ORGANISM: Artificial Sequence
<220> FEATURE:
<223> OTHER INFORMATION: TBX6 R primer

<400> SEQUENCE: 74
cctcccagct ttggtgatga t    21

<210> SEQ ID NO 75
<211> LENGTH: 19
<212> TYPE: DNA
<213> ORGANISM: Artificial Sequence
<220> FEATURE:
<223> OTHER INFORMATION: TBX10 F primer

<400> SEQUENCE: 75
cctcggcata cttgcaccc    19

<210> SEQ ID NO 76
<211> LENGTH: 21
<212> TYPE: DNA
<213> ORGANISM: Artificial Sequence
<220> FEATURE:
<223> OTHER INFORMATION: TBX10 R primer

<400> SEQUENCE: 76
attcctccca cagaggcttc a    21

<210> SEQ ID NO 77
<211> LENGTH: 20
<212> TYPE: DNA
<213> ORGANISM: Artificial Sequence
<220> FEATURE:
<223> OTHER INFORMATION: TBX18 F primer

<400> SEQUENCE: 77 gccccctgctg actattctgc    20

<210> SEQ ID NO 78
<211> LENGTH: 21
<212> TYPE: DNA
<213> ORGANISM: Artificial Sequence
<220> FEATURE:
<223> OTHER INFORMATION: TBX18 R primer

<400> SEQUENCE: 78
ctgcatggat aagctggtct g    21

<210> SEQ ID NO 79
<211> LENGTH: 21
<212> TYPE: DNA
<213> ORGANISM: Artificial Sequence
<220> FEATURE:
<223> OTHER INFORMATION: TBX19 F primer

<400> SEQUENCE: 79
aagaatggca gacggatgtt t    21

<210> SEQ ID NO 80
<211> LENGTH: 20
<212> TYPE: DNA
<213> ORGANISM: Artificial Sequence
<220> FEATURE:

-continued

<223> OTHER INFORMATION: TBX19 R primer

<400> SEQUENCE: 80
ccgggtgaat gtagacgcag                    20

<210> SEQ ID NO 81
<211> LENGTH: 19
<212> TYPE: DNA
<213> ORGANISM: Artificial Sequence
<220> FEATURE:
<223> OTHER INFORMATION: RUNX2 F primer

<400> SEQUENCE: 81
cggcaaaatg agcgacgtg                     19

<210> SEQ ID NO 82
<211> LENGTH: 19
<212> TYPE: DNA
<213> ORGANISM: Artificial Sequence
<220> FEATURE:
<223> OTHER INFORMATION: RunX2 R primer

<400> SEQUENCE: 82
caccgagcac aggaagttg                     19

<210> SEQ ID NO 83
<211> LENGTH: 20
<212> TYPE: DNA
<213> ORGANISM: Artificial Sequence
<220> FEATURE:
<223> OTHER INFORMATION: LMO2 F primer

<400> SEQUENCE: 83
ggccatcgaa aggaagagcc                    20

<210> SEQ ID NO 84
<211> LENGTH: 21
<212> TYPE: DNA
<213> ORGANISM: Artificial Sequence
<220> FEATURE:
<223> OTHER INFORMATION: LMO2 R primer

<400> SEQUENCE: 84
ggcccagttt gtagtagagg c                  21

<210> SEQ ID NO 85
<211> LENGTH: 21
<212> TYPE: DNA
<213> ORGANISM: Artificial Sequence
<220> FEATURE:
<223> OTHER INFORMATION: TAU F primer

<400> SEQUENCE: 85
cccctggagt tcacgtttca c                  21

<210> SEQ ID NO 86
<211> LENGTH: 20
<212> TYPE: DNA
<213> ORGANISM: Artificial Sequence
<220> FEATURE:
<223> OTHER INFORMATION: TAU R primer

<400> SEQUENCE: 86
gcgagctttg agttgaggga                    20

US 8,486,701 B2

ETS2 AND MESP1 GENERATE CARDIAC PROGENITORS FROM FIBROBLASTS

This application claims priority to U.S. Provisional Patent Application Ser. No. 61/339,509, filed on Mar. 5, 2010, entitled ETS2 AND MESP1 GENERATE CARDIAC PROGENITORS FROM FIBROBLASTS, the entire content of which is hereby incorporated by reference.

FIELD OF THE INVENTION

One aspect of the present invention relates generally to the field of cell differentiation, and more specifically to a strategy for cardiovascular tissue regeneration via the isolation, renewal, and directed differentiation, of fibroblasts into specific mature cardiac, pacemaker, smooth muscle, and endothelial cell types.

BACKGROUND

Damage to mammalian heart tissue frequently results in the loss of large numbers of cardiac cells, including mature cardiac cells, pacemaker cells, smooth muscle, and endothelial cells. Although there is some indication that cardiac cells can be regenerated in humans (Bergmann et al., 2009), the mechanism is not well understood and the process does not appear to proceed rapidly enough to repair common types of cardiac damage such as ischemia, infarction, trauma, or injury due to toxins or viral infections. Therefore, a central goal of experimental cardiac medicine has been the development of a means for regenerating cardiac cells which have been lost due to cardiac damage. Studies of the mechanisms behind the embryonic cardiogenesis have been conducted, with the aim of replicating cardiogenesis in vitro or in vivo for the purposes of regenerating damaged tissue.

Recent research has identified multipotent (Isl1+) cardiovascular progenitor (MICP) cells, which are capable of differentiating to form mature cardiac tissue. MICP cells derived from embryonic stem (ES) cells which can give rise to endothelial, cardiac, and smooth muscle cells, have been isolated (Moretti et al., 2006). Genetic studies have shown that these MICP cells express Isl1, Nkx2.5 and Flk1.

Model systems for investigating cardiogenesis include the ascidian *Ciona intestinalis* (Beh et al., 2007). Lineage studies have shown that the adult *Ciona* heart is derived from two founder cells that express Ci-Mesp, a basic helix-loop-helix (bHLH) transcription factor, and also Ci-Ets1/2 (Imai et al., 2004; Satou et al., 2004). In addition, ascidian orthologs of the conserved heart specification genes NK4 (tinman Nkx2.5), GATAa (pannier/GATA4/5/6), Hand and Hand-like (Imai et al., 2003; Davidson, 2007; Davidson and Levine, 2003; Satou et al., 2004) are expressed. Ci-Mesp-knockdown embryos did not develop heart primordia, and target inhibition of Ets1/2 activity also blocked heart specification and the expansion of the heart field. Similarly, murine homologues of Ci-Mesp, Mesp1 and Mesp2 are expressed in the early mesoderm fated to become cranio-cardiac mesoderm (Saga et al., 2000). Only the Mesp1/Mesp2 double-knockout mouse lacked any cardiac mesoderm (Saga et al., 1999; Kitajima et al., 2000), indicating a role for these genes in directing the appearance of cardiac progenitors in higher vertebrates. Redundancies of Mesp genes have made further study in embryos a daunting task.

What is needed in the art is a method of inducing cardiogenesis for the purpose of regenerating cardiac cells for the use in the treatment of damaged cardiac tissue. Reprogramming of human somatic cells into pluripotent cells by a limited number of transcriptional factors important for maintaining self renewal and pluripotency has been reported by Yamanaka's, Thomson's and Daley's groups (Takahashi et al., 2007; Yu et al., 2007; Park et al., 2008). One aspect of the present invention provides a means of reprogramming the somatic cells and directed differentiation into cardiac progenitor cells. Therefore, one embodiment of this application provides a way to test a unique regulatory paradigm that ETS2 and Mesp1 are transformative, and unlike NKX2.5 and ISL1, convert non-embryonic normal human dermal fibroblasts (NHDFs) into primary cardiac progenitors. Another aspect of the present application was to elucidate the role of Mesp1 in the regulatory hierarchy directing the appearance of cardiac progenitors.

SUMMARY

One embodiment of the present invention relates to the modulation of cell differentiation capabilities using heterologous gene expression. Some embodiments of the invention relate to a method for inducing a cardiac progenitor cell by delivering a reprogramming factor to the cell, wherein the reprogramming factor comprises ETS2 or a combination of ETS2 and Mesp1.

A further embodiment of the present invention provides a cardiac progenitor cell which has been induced by reprogramming a somatic cell, wherein reprogramming comprises delivery of a reprogramming factor comprising the ETS2 gene to the somatic cell. The somatic cell may be a normal human dermal fibroblast (NHDF), and the reprogramming factor may be ETS2 or Mesp1, or a combination thereof.

Still a further embodiment of the present invention provides a method of reprogramming a somatic cell to produce a cardiac progenitor cell, wherein reprogramming comprises delivery of a reprogramming factor comprising the ETS2 gene to the somatic cell. The somatic cell may be an NHDF, and the reprogramming factor may be ETS2 or Mesp1, or a combination thereof.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF PREFERRED EMBODIMENTS

Figure 1:
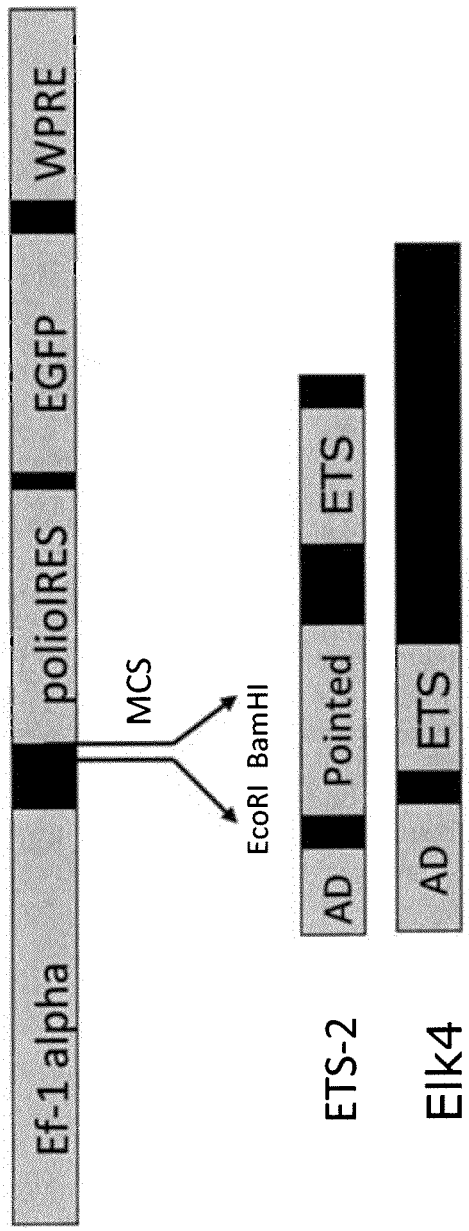
FIG. 1 shows a schematic map of lentivirus with the insertion of ETS2 and ELK4 full length DNA coding sequences. Functional elements and abbreviations: constitutive Ef-1alpha promoter, multiple cloning sites (MCS), independent ribosome entry site (IRES) from human polio virus, coding sequence for enhanced green fluorescence protein (eGFP), Woodchuck Hepatitis Virus Posttranscriptional Regulatory Element (WPRE), activation domain (AD), DNA-binding ETS domain. These plasmids were generated by standard recombinant DNA cloning techniques and then used to make lentiviruses to infect normal human dermal fibroblasts (NHDFs)

One embodiment of the present invention relates to the modulation of cell differentiation using heterologous gene expression. Some embodiments of the invention relate to a method for inducing a cardiac progenitor cell by delivering a reprogramming factor to the cell, wherein the reprogramming factor comprises ETS2 or a combination of ETS2 and Mesp1.

An embodiment of the present invention provides a method for inducing a cardiac progenitor cell by reprogramming a somatic cell, wherein reprogramming comprises delivery of a reprogramming factor comprising a single heterologous gene to the somatic cell. The somatic cell may be a fibroblast, preferably a normal human dermal fibroblast. The heterologous gene may be ETS2. The heterologous gene may comprise the human ETS2 coding sequence (SEQ ID NO:9) or the ETS2 gene (SEQ ID NO:7), or the heterologous gene may encode the human ETS2 protein sequence (SEQ ID NO:8). The induced stem-like cell may exhibit cardiogenesis or other characteristics of cardiac progenitor cells as a result of programming, including the expression of cardiac progenitor factors such as NKX2.5, ISL1, MEF2C, dHAND and GATA4, or rhythmic beating.

Another embodiment of the present invention provides a method for inducing a cardiac progenitor cell by reprogramming a somatic cell, wherein reprogramming comprises delivery of a reprogramming factor comprising two heterologous genes to the somatic cell. The somatic cell may be a fibroblast, preferably a normal human dermal fibroblast. The heterologous genes may be ETS2 and Mesp1. The heterologous genes may comprise the human ETS2 coding sequence (SEQ ID NO:9), the ETS2 gene (SEQ ID NO:7), or a DNA sequence encoding the human ETS2 protein sequence (SEQ ID NO:8) and the mouse Mesp1 coding sequence (SEQ ID NO:6), the mouse Mesp1 gene (SEQ ID NO:4), or a DNA sequence encoding the mouse Mesp1 protein sequence (SEQ ID NO:5). The induced stem-like cell may exhibit cardiogenesis or other characteristics of cardiac progenitor cells as a result of programming, including the expression of cardiac progenitor factors such as NKX2.5, ISL1, MEF2C, dHAND and GATA4, or rhythmic beating.

Yet another embodiment of the present invention, reprogramming of a somatic cell, may be accomplished by delivering a reprogramming factor to the somatic cell using a recombinant vector. The reprogramming factor may also be delivered using a lentiviral transduction system to express the reprogramming factor in the somatic cell. In these embodiments, the reprogramming factor may be ETS2 and Mesp1.

A further embodiment of the present invention provides a somatic cell which has been reprogrammed, wherein reprogramming comprises delivery of a reprogramming factor comprising a single heterologous gene or multiple heterologous genes to the somatic cell. The somatic cell may be a fibroblast, preferably a normal human dermal fibroblast. The heterologous genes may be ETS2 or the multiple heterologous genes may be ETS2 and Mesp1. The induced stem-like cell may exhibit cardiogenesis or other characteristics of cardiac progenitor cells as a result of programming, including the expression of cardiac progenitor factors such as NKX2.5, ISL1, MEF2C, dHAND and GATA4, or rhythmic beating.

Example 1

Selection of a Reprogramming Factor

It was noted that the ETS domain (FIG. 1), a highly conserved DNA-binding domain, is capable of binding to a 5'-GGA(A/T)-3' DNA core motif found on the promoters of many stem cell marker genes. The expression of ETS2 is linked to immortalization of cells, mediation of oncogenesis, and enhancement of telomerase activity.

Figure 2:
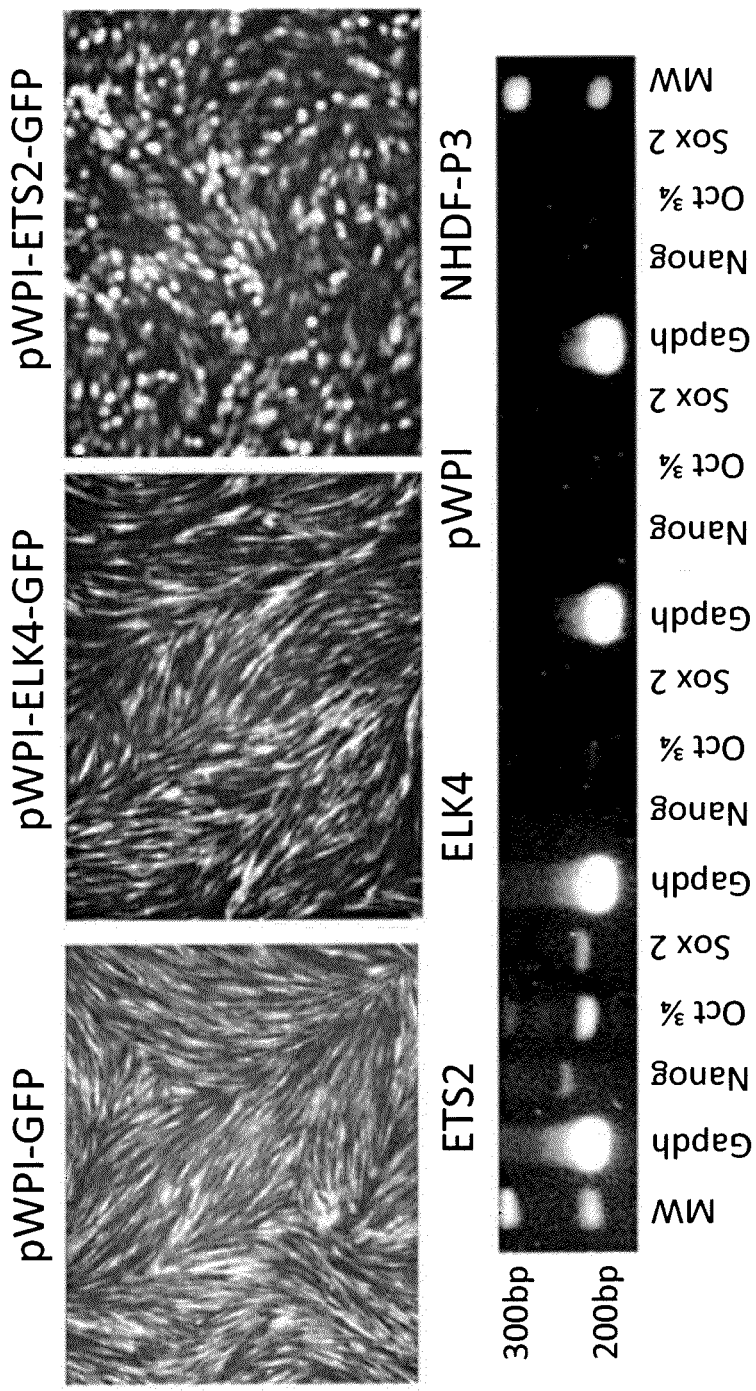
FIG. 2 shows (top panel) NHDFs treated with empty lentivirus (pWPI-GFP), pWPI-ELK4-GFP lentivirus, or pWPI-ETS2-GFP lentivirus, and (bottom panel) expression levels of GAPDH, NANOG, OCT3/4, SOX2 in cells infected with empty virus, virus carrying ETS2, virus carrying ELK4, or uninfected NHDF passage 3 (NHDF-P3)
Figure 3:
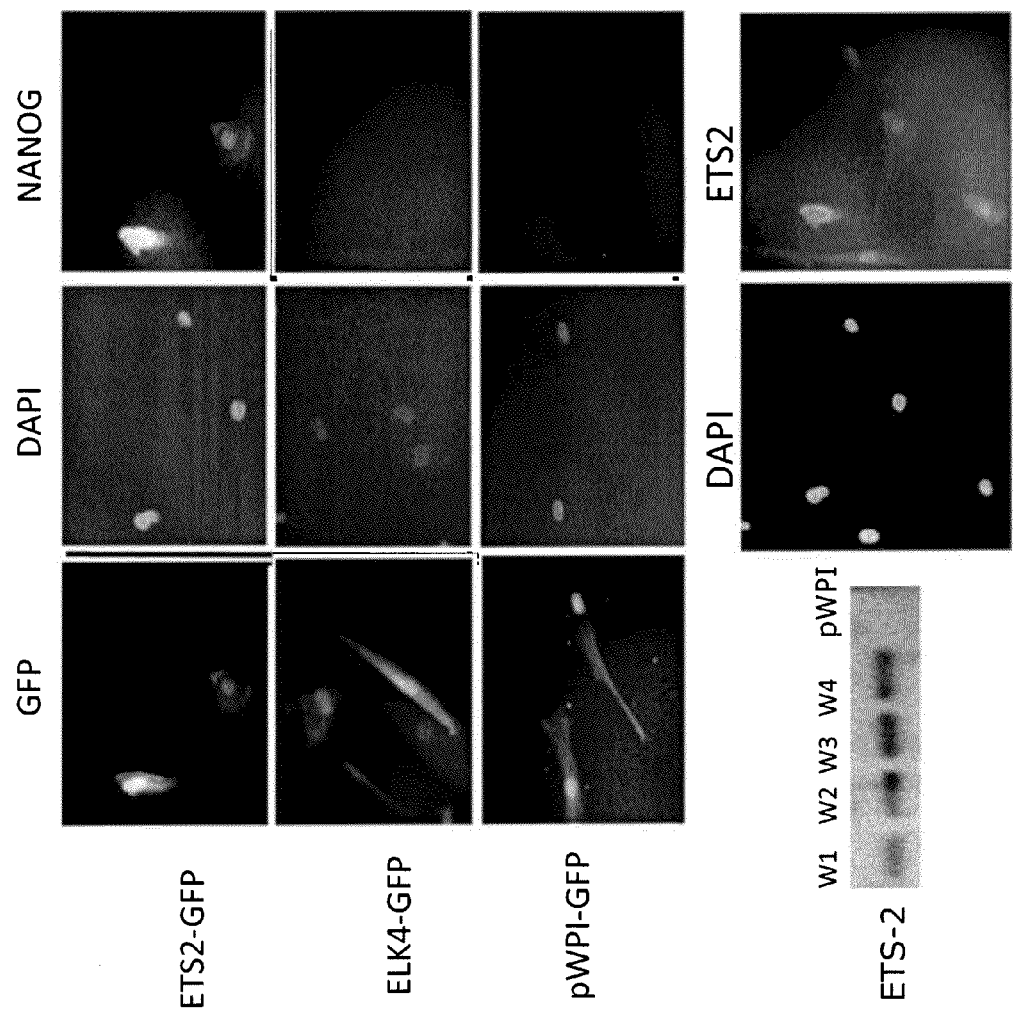
FIG. 3 shows immunofluorescence staining with antibody to a stem cell marker NANOG in NHDF-P3 cells infected with lentivirus carrying ETS2, but not ELK4 or empty vector (top panel). A protein blot using anti-ETS2 antibody revealed expression of ETS2 in NHDFs infected with lentivirus carrying ETS2 for 4 weeks, while NHDFs infected with empty lentivirus showed no expression (bottom left panel). Immunofluorescence staining with anti-ETS2 antibody confirmed the induced expression in the cells infected with ETS2 lentivirus (bottom right panel)

ETS2 and ELK4, an ETS family gene homologous to ETS2 in its DNA-binding region, were transduced using lentiviral vectors into NHDF-P3. Within one week, fibroblasts transduced with lentiviral vectors containing ETS2 were replaced with highly proliferative small rounded cells. These highly proliferative cells were not observed in controls transduced with empty lentivirus, or in the fibroblasts transduced with lentiviral vectors containing ELK4 (FIG. 2-3).

Example 2

Lentiviral Transduction System

FIG. 1 shows a schematic map of lentivirus with the insertion of ETS2 (SEQ ID NO:9) and ELK4 (SEQ ID NO:3) DNA coding sequences. Note that only ETS2 has a pointed domain. These plasmids were used to make lentiviruses to infect NHDFs. The ETS2 full-length sequence (SEQ ID NO:7) comprises an ETS2 coding sequence (SEQ ID NO:9) encoding an ETS2 protein sequence (SEQ ID NO:8). The ELK4 full-length sequence (SEQ ID NO:1) comprises an ELK4 coding sequence (SEQ ID NO:3) encoding a protein sequence (SEQ ID NO:2).

The empty lentivirus vector pWPI-eGFP was a gift from Dr. D. Trono (Ecole Polytechnique Fédérale de Lausanne, Switzerland). cDNA for cloning the human ETS2 and ELK4 genes (Clone IDs 3852274 and 4364006) were obtained from Open Biosystems, whereas the Mesp1 cDNA was a gift from Dr. Y. Saga (National Institute of Genetics, Mishima, Japan). The consensus Kozak sequence for initiation of protein translation and the epitope HA-tag were added respectively to the 5'- and 3'-ends of ETS2, ELK4 and Mesp1 coding sequences by PCR cloning.

Lentivirus packing and infection proceeded as follows: Seeded 293FT cells in 6-cm dishes were transfected with either pWPI-eGFP, or pWPI-ELK4-eGFP (human ELK4 coding sequence, SEQ ID NO:3), or pWPI-ETS2-eGFP (human ETS2 coding sequence, SEQ ID NO:9), or pWPI-Mesp1-eGFP (mouse MesP1 sequence, SEQ ID NO:6), or SMPU-alphaMHC/puro-Rex1/Blast (gift from Dr. M. Mercola, Burnham Institute for Medical Research, La Jolla, Calif.). 4.5 ug of either construct was mixed in a solution of 458 ul of serum-free Dulbecco-modified Eagle medium (DMEM) and 27.5 ul of Fugene (Roche), 2.8 ug of packing vector psPAX2 and 1.9 ug of envelope vector pMD2.G for 25 min at room temperature. Afterwards the mix was added to 293FT cells grown in DMEM, phenol red-free (Invitrogen) supplemented with 10% FBS (heat-inactivated), 0.1 mM MEM non-essential amino acids, 1 mM sodium pyruvate and 6 mM L-glutamate. After 24-26 hrs in culture, medium with viral particles was collected for 3 days and used for infection.

Collected medium was used to infect NHDFs grown in Fibroblast Basal Medium (FBM, Lonza) until 80% confluency. Before transfection, cells were reseeded in 6-cm Petri dishes at a density of $2.5 \times 10^6$ cell/dish, the medium was changed to StemPro and the viral particles and polybrene (8 ug/ml final concentration) were added. To increase the efficiency of infection, the procedure was repeated within 48 hours. All cells were grown at 37° C. and 5% $CO_2$.

Example 3

Gene Expression in Reprogrammed Cells

FIG. 2 shows that ETS2 lentivirus but not ELK4 lentivirus induced stem cell appearance and the induction of stem cell marker proteins, NANOG, OCT3/4 and SOX2 within 7 days of culture. The top panel of FIG. 2 shows NHDFs (Lonza, USA, cc-2509) grown under FBM, supplemented (supplements provided by Lonza) with hFGF-beta, insulin, gentamycin/amphotericin and 2% FBS, to a confluence of ca. 80% before viral infection. Empty pWPI-eGFP and pWI-ELK4-eGFP and pWPI-ETS2-eGFP lentiviruses were used to separately infect NHDF-P3. Infected and non-infected NHDF-P3 cells were grown under human induced pluripotent medium StemPro hES SFM (Invitrogen) over collagen-coated Petri dishes for 7 days. The green fluorescent protein cloned into the lentiviral vectors was expressed in the infected cells, as revealed by the green fluorescence microscopy. During this culture period, morphological changes were observed in which ETS2-infected NHDFs changed their appearance from elongated pleomorphic fibroblastic shapes to rounded "stem-like cells". In comparison, NHDFs infected with an empty or ELK4 lentiviral vectors did not alter cell shape.

The bottom panel of FIG. 2 shows the reverse transcription PCR (RT-PCR) analysis of reprogrammed cells. Cells were washed in chilled PBS and RNA was isolated with Qiagen RNeasy Kit. RNA was transcribed using MMLV reverse transcriptase (Invitrogen), and PCR amplification (30 cycles) was performed for GAPDH, NANOG, OCT3/4, SOX2 (refer to Table 1 for primer sets) using LA16 polymerase mix. This enzyme mix was prepared using 15 ul of KlenTaq1 (25 units/ul, Ab Peptides. St Louis, Mo.) and 1 ul Pfu (2.5 units/ul, Stratagene, La Jolla, Calif.). Amplified DNA samples were then electrophoresed on 2% agarose gel and ethidium bromide staining revealed the induced expression of stem cell marker genes NANOG, OCT3/4 and SOX2 in ETS2-infected cells but not in NHDF-P3 or cells infected with either ELK4 or empty lentiviruses.

TABLE 1

Primers for Cardiac Progenitor Study

| Primer | SEQ ID NO | Seq | Product size |
|---|---|---|---|
| GapdhFP crtl exp | 11 | TGTTGCCATCAATGACCCCTT | 202 |
| GapdhRP ctrl exp | 12 | CTCCACGACGTACTCAGCG | |
| hNanogFP ctrl exp | 13 | CAGAAGGCCTCAGCACCTAC | 225 |
| hNanogRP ctrl exp | 14 | TATAGAAGGGACTGTTCCAGGC | |
| hOct 3/4FP ctrl exp | 15 | CTTGAATCCCGAATGGAAAGGG | 206 |
| hOct 3/4 RP ctrl exp | 16 | CCTTCCCAAATAGAACCCCCA | |
| Sox2 HPB F | 17 | TGGACAGTTACGCGCACAT | 215 |
| Sox2 HPB R | 18 | CGAGTAGGACATGCTGTAGGT | |
| hRex1FP ctrl exp | 19 | GCTGACCACCAGCACACTAGGC | 298 |
| hRex1RPctrl exp | 20 | TTTCTGGTGTCTTGTCTTTGCCCG | |

TABLE 1-continued

Primers for Cardiac Progenitor Study

| Primer | SEQ ID NO | Seq | Product size |
|---|---|---|---|
| c-Myc HPB F | 21 | AGGCGAACACACAACGTCTT | |
| c-Myc HPB R | 22 | TTGGACGGACAGGATGTATGC | |
| hKlf4FP ctrl exp | 23 | ATGGCTGTCAGCGACGCGCTGCTC | 293 |
| hKlf4RP ctrl exp | 24 | CGTTGAACTCCTCGGTCTCTCTCC | |
| Nkx 2.5 FP | 25 | ccctgaccgatcccacctcaac | 358 |
| Nkx 2.5 RP | 26 | GGCGGGCGACGGCGAGATAGC | |
| Mesp 1 FP | 27 | tcgaagtggttccttggcagac | 162 |
| Mesp 1 RP | 28 | CCTCCTGCTTGCCTCAAAGTGTC | |
| Mesp 2 FP | 29 | CGCTGCGCCTGGCCCATCCGCTACAT | 113 |
| Mesp 2 RP | 30 | GCCCCAAGGGGACCCCGCGAC | |
| Mef2c FP | 31 | gcaccagtgcagggaacggg | 202 |
| Mef2c RP | 32 | GACTGAGCCGACTGGGAGTTA | |
| Sox 17 FP | 33 | gcggcgcaagcaggtgaag | 205 |
| Sox 17 RP | 34 | ACTCTGGCAGTCGCGGTAGTGGC | |
| FoxA2 FP | 35 | ctgaagccggaacaccactacgc | 214 |
| FoxA2 RP | 36 | TCCAGGCCCGTTTTGTTCGTGAC | |
| FGF8 FP | 37 | agctcagccgccgcctcatccg | 313 |
| FGF8 RP | 38 | AGCCCTCGTACTTGGCATTCTGC | |
| MyoD FP | 39 | AggggctaggttcagctttctcG | 240 |
| MyoD RP | 40 | CTCCTGCTCTGGCAAAGCAACTC | |
| BMP2 HBP FP | 41 | ACCTTTATGGAGGGAAACCCA | 201 |
| BMP2 HBP RP | 42 | CCGGATCTGGTTCAAGCATGA | |
| hTert HBP FP | 43 | AACCTTCCTCAGCTATGCCC | 210 |
| hTert HBP RP | 44 | GCGTGAAACCTGTACGCCT | |
| Islet-1 HPB F | 45 | GTGGAGAGGGCCAGTCTAGG | 250 |
| Islet-1 HPB R | 46 | CCGTCATCTCTACCAGTTGCT | |
| Troponin T HPB F | 47 | GAGTTGCAGGCGCTGATTG | 229 |
| Troponin T HPB R | 48 | TCTGGATGTAACCCCCAAAATG | |
| Dhand HPB F | 49 | ATGAGTCTGGTAGGTGGTTTCC | 205 |
| Dhand HPB R | 50 | CATACTCGGGGCTGTAGGACA | |
| T HPB F | 51 | GATCACGCAGCTCAAGATTGC | 230 |
| T HPB R | 52 | TCTCTGGTGTGTTCCTAGACG | |
| T5 HPB F | 53 | CACTTCTCCGCTCACTTCACC | 210 |
| T5 HPB R | 54 | TGGCACGCCATGAGAGTAGA | |
| ETS-2 HPB F | 55 | AAAGCTACCTTCAGTGGCTTC | 225 |
| ETS-2 HPB R | 56 | AATGTCACCCACAAAGTCAGG | |
| Dkk-1 FP | 57 | ATTCCAACGCTATCAAGAACC | 384 |
| Dkk-1 RP | 58 | CCAAGGTGCTATGATCATTACC | |
| TBX 20 FP | 59 | tccagattctccttttaccg | 190 |
| TBX 20 RP | 60 | ttcagacttcaggttgagca | |
| SM actin HBP F | 61 | CGGTGCTGTCTCTCTATGCC | 156 |
| SM actin HBP R | 62 | CACGCTCAGTCAGGATCTTCA | |
| hGATA1 F | 63 | AGAAGCGCCTGATTGTCAGTA | 229 |
| hGATA1 R | 64 | AGAGACTTGGGTTGTCCAGAA | |
| hGTAT2 F | 65 | GGCCCACTCTCTGTGTACC | 243 |
| hGATA2 R | 66 | CATCTTCATGCTCTCCGTCAG | |
| TBX3-1 F | 67 | GTGTCTCGGGCCTGGATTC | 164 |
| TBX3-1 R | 68 | ACGTGTAGGGGTAAGGGAACA | |
| TBX3-2 F | 69 | TTAAAGTGAGATGTTCTGGGCTG | 298 |
| TBX3-2 R | 70 | ACTATAATTCCCCTGCCACGTA | |
| TBX4 F | 71 | TGACCATCGCTACAAGTTCTGT | 163 |
| TBX4 R | 72 | GGTGGTTGTTTGTCAGCTTCAG | |
| TBX6 F | 73 | ACACCCCTAAACTGGATTGCT | 229 |
| TBX6 R | 74 | CCTCCCAGCTTTGGTGATGAT | |
| TBX10 F | 75 | CCTCGGCATACTTGCACCC | 208 |
| TBX10 R | 76 | ATTCCTCCCACAGAGGCTTCA | |
| TBX18 F | 77 | GCCCCTGCTGACTATTCTGC | 227 |
| TBX18 R | 78 | CTGCATGGATAAGCTGGTCTG | |
| TBX19 F | 79 | AAGAATGGCAGACGGATGTTT | 204 |
| TBX19 R | 80 | CCGGGTGAATGTAGACGCAG | |
| RUNX2 F | 81 | CGGCAAAATGAGCGACGTG | 268 |
| RunX2 R | 82 | CACCGAGCACAGGAAGTTG | |
| LMO2 F | 83 | GGCCATCGAAAGGAAGAGCC | 221 |
| LMO2 R | 84 | GGCCCAGTTTGTAGTAGAGGC | |
| TAU F | 85 | CCCCTGGAGTTCACGTTTCAC | 240 |
| TAU R | 86 | GCGAGCTTTGAGTTGAGGGA | |

Example 4

Stem Cell Marker Proteins in Reprogrammed Cells

FIG. 3 shows immunofluorescence staining of infected NHDF-P3 with antibody to the stem cell marker NANOG. Induced NANOG staining is revealed in ETS2-infected cells but not in ELK4- or empty vector-infected cells. Also, a protein blot using ETS2-specific antibody revealed its expression in cells infected with ETS2 lentivirus but not in NHDFs infected with empty lentivirus.

Figure 4:
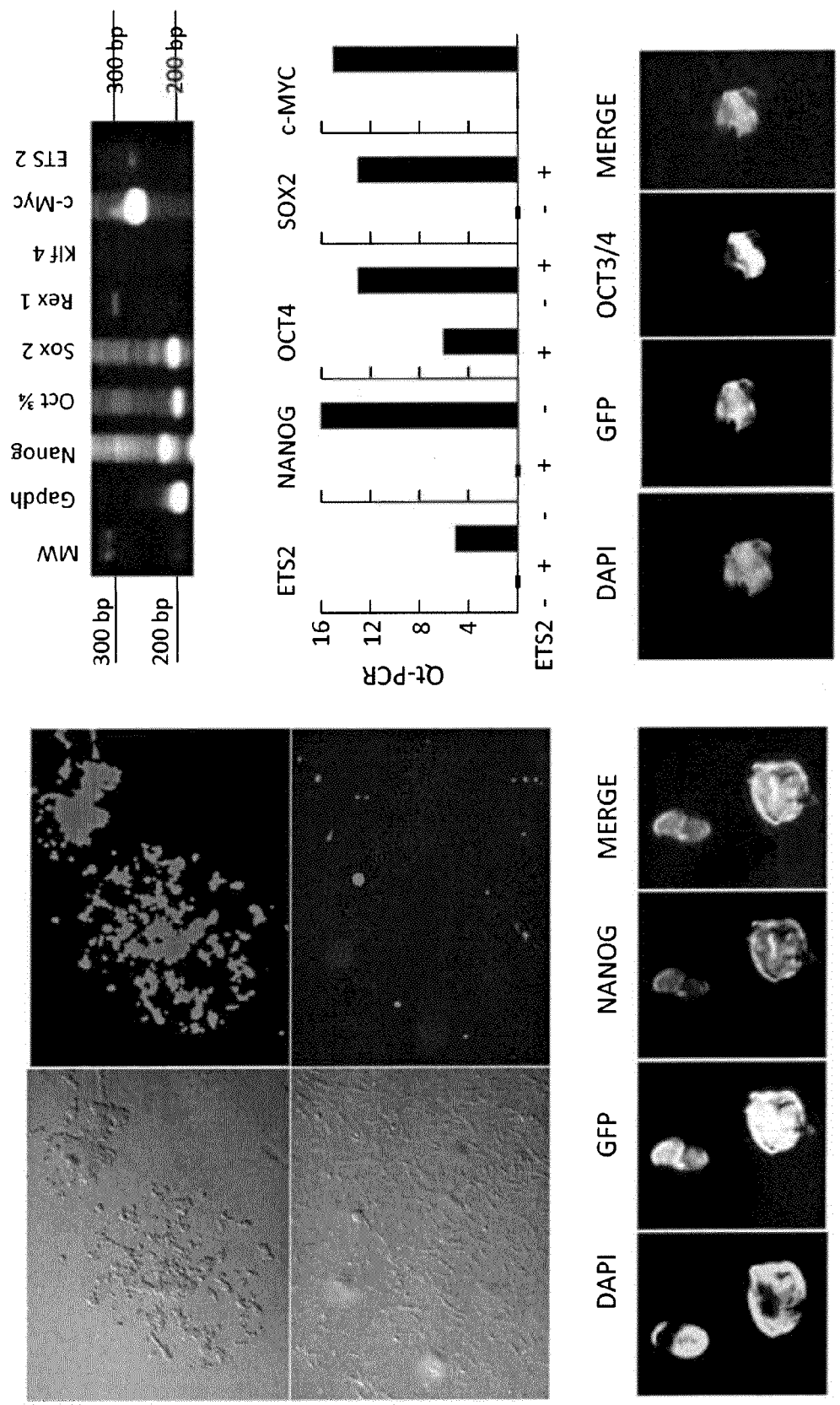
FIG. 4 shows induction of stem cell markers NANOG, OCT3/4, SOX2, REX1 and c-MYC in stem cell-like colonies after 4 weeks in culture. The fluorescent colors (colors not shown in the figures) are as follows: DAPI (blue), GFP (green), NANOG and OCT3/4 (red), a mixture of all three colors is observed in the "merge" panels. Color fluorescent images are available upon request.

FIG. 4 shows ETS2 lentivirus-induced stem cell-like colonies and the induction of stem cell marker proteins NANOG, OCT3/4, SOX2, REX1 and c-MYC after 4 weeks in culture. The top left panel shows that NHDFs infected with ETS2 virus converted to colonies of small rounded cells highly reminiscent of cultured murine and human embryonic stem cells. Note that colonies were GFP-labeled through the infection with ETS2 lentivirus. Non-infected fibroblasts failed to round and did not stain for GFP or form cellular colonies.

The right top panel of FIG. 4 shows the expression of stem cell marker genes NANOG, OCT3/4, SOX2, REX1, KLF4 and c-MYC in ETS2-induced cellular colonies analyzed by RT-PCR. Underneath is graphic representation of quantitative RT-PCR for NANOG, OCT3/4, SOX2 and c-MYC in ETS2-infected cells.

The lower panels of FIG. 4 confirm the presence of NANOG and OCT3/4 proteins in ETS2-induced cellular colonies by immunofluorescence staining with specific antibodies.

Example 5

Characteristics of Cells Transduced with ETS2

Figure 5:
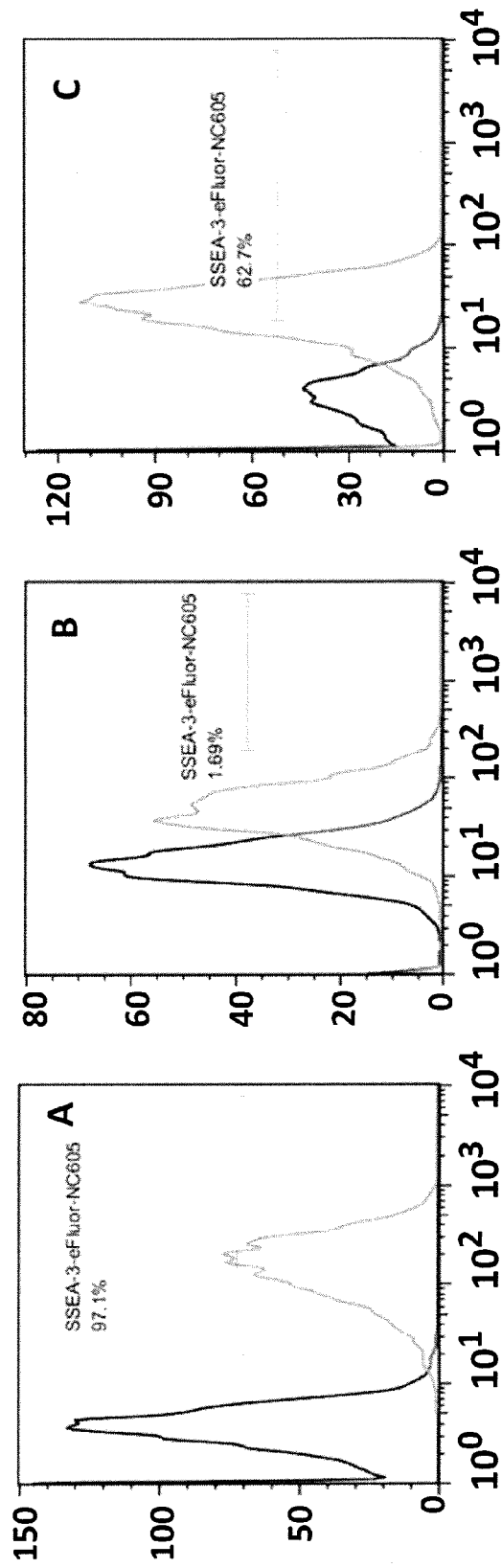
FIG. 5 shows flow cytometry demonstrating the percent of H9 human embryonic stem cells (A), uninfected NHDFs (B), or ETS2-infected cells (C) that stained for the stem cell surface marker SSEA-3. Negative controls, black lines; SSEA-3 staining, gray lines.

FIG. 5 shows that approximately 97% of H9 human embryonic stem cells stained for the stem cell surface marker SSEA-3 (Panel A). Over 60% of ETS2-infected cells also displayed surface marker SSEA-3 (Panel C), in comparison to less than 2% staining of the NHDFs infected with empty lentivirus (Panel B). Thus, ETS2 efficiently converted NHDFs into cells with the SSEA-3 surface marker resembling human embryonic stem cells.

Flow cytometry was done using a BD Biosciences LSR II analyzer. Confluent colony-forming cells were dissociated by trypsin, washed with PBS and diluted to a concentration of $5 \times 10^6$ cells/ml PBS in 8 samples (100 ul each). Thereafter 10 ul of normal human serum was used for blocking for 5 min. Antibodies to SSEA-3-PE (Becton Dickinson) were diluted and added according to manufacturer's specifications, and incubated for 1 hr at 4° C. Then 400 ul PBS was added and the mixture was spun down and half of the supernatant was removed and 200 ul PBS was added and assayed by flow cytometry.

Figure 6:
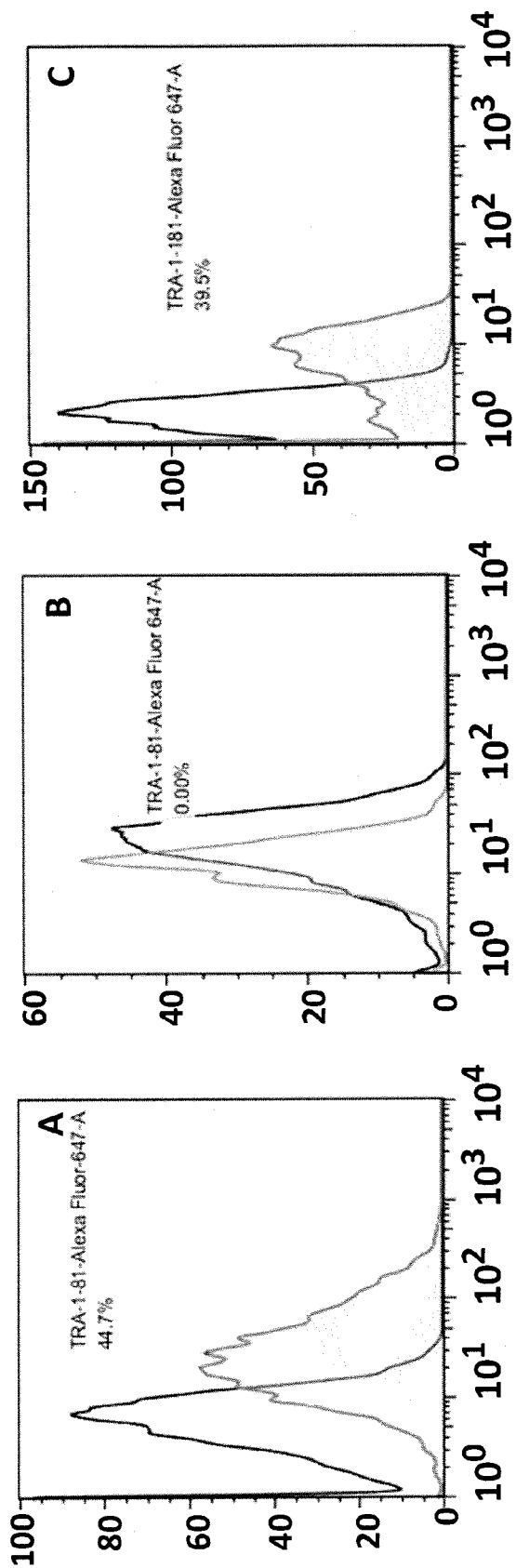
FIG. 6 shows flow cytometry demonstrating the percent of H9 human embryonic stem cells (A), uninfected NHDFs (B), or ETS2-infected cells (C) that stained for the stem cell surface marker Tra-1-81. Negative controls, black lines; Tra-1-81 staining, gray lines.

FIG. 6 shows flow cytometry of cells stained for the stem cell surface marker Tra-1-81 performed as for SSEA-3. Approximately 45% of H9 human embryonic stem cells stained for Tra-1-81 (Panel A). No Tra-1-81 staining (Panel B) was detected for NHDFs infected with empty lentivirus (not carrying a heterologous gene). Infection with ETS2 virus gave rise to approximately 39% cells displaying embryonic stem cell marker Tra-1-81 (Panel C). This indicates that ETS2 efficiently converted NHDFs into cells with the Tra-1-81 surface marker resembling human embryonic stem cells.

OCT3/4, NANOG and SOX2 gene transcripts were observed only after NHDF-P3 were transduced with lentiviral vector containing ETS2 but not after transduction with empty lentivector or vector containing ELK4. OCT3/4, NANOG and SOX2 transcripts were visualized (FIG. 2) and NANOG induction was visualized using immunofluorescence (FIG. 3).

Lentiviral transduction of HNDF-P3 cells with ETS2 resulted in whole populations which showed robust ETS2 expression over 4 weeks visualized by protein blots (FIG. 3). These ETS2-transduced cells formed large green fluorescent colonies similar to those of pluripotent ES and/or induced pluripotent stem (iPS) cells.

Reprogramming of fibroblasts with ETS2 resulted in strong expression of the pluripotent marker genes NANOG, OCT3/4, SOX2 and c-MYC measured by both RT-PCR and quantitative PCR and immunostaining. Additionally, flow cytometry shows that ETS2 efficiently converted NHDFs into cells with surface markers SSEA-3 and Tra-1-81 resembling human embryonic stem cells. Thus, these ETS2-treated human fibroblast cells resemble iPS cells in their ability to express pluripotent stem cell marker proteins. These cells were therefore named "EPS" cells.

Example 6

Combination of ETS2 and Mesp1 Induces De Novo Cardiac Progenitor Program in Fibroblasts Next, EPS cells were subjected to lentiviral transduction with mouse Mesp1. The resulting EPS cells expressing Mesp1 could be induced to form embryoid bodies using protocols for forming embryoid bodies from ES cells. Plated cellular aggregates were further treated with activin and BMP4 for 4 days and then examined at 10 days. Constitutive expression of stem cell markers continued even after the transduction with Mesp1 and addition of growth factor morphogens.

Figure 7:
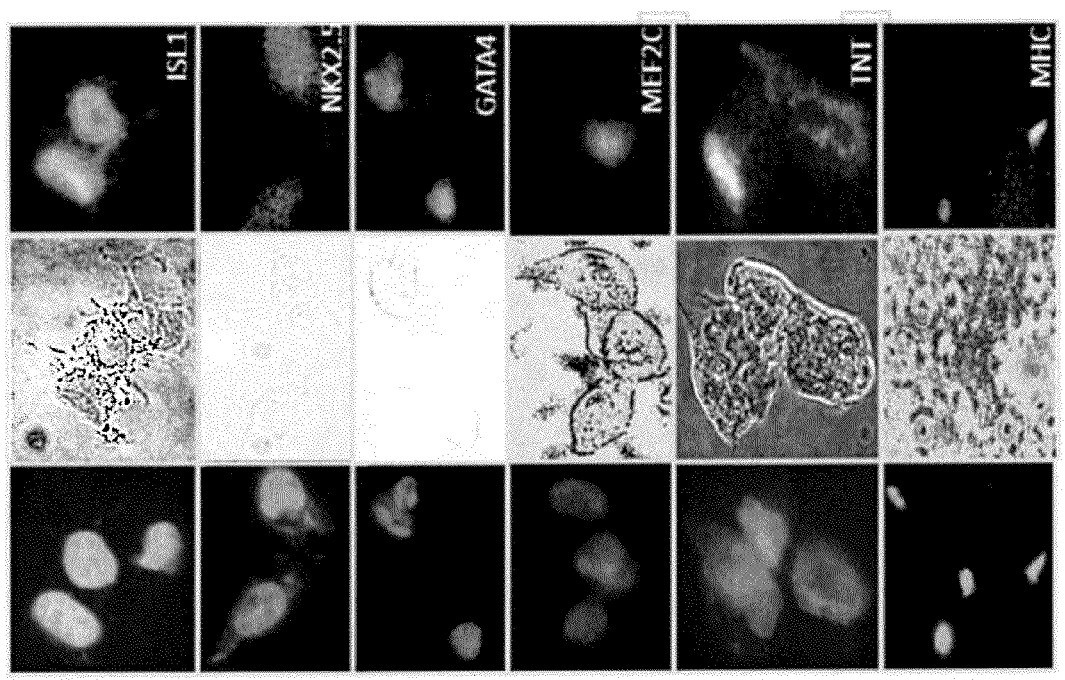
FIG. 7 shows images of EPS cells after infection with Mesp1 lentivirus. Cells were stained with DAPI to visualize nuclei (left panels) and with specific antibodies to ISL1, NKX2.5, GATA4, MEF2C, TNT and MHC3 to visualize indicated cardiac progenitor proteins (right panels). Panels in the middle show phase contrast images of cells. The fluorescent colors are as follows: DAPI (blue), protein-specific staining (red). Color fluorescent images are available upon request.

Robust induction of the cardiac progenitor factors ISL1, NKX2.5, GATA4, MEF2C, TNT and MHC was observed by immunostaining only in the EPS cells infected with lentivirus expressing Mesp1. FIG. 7 shows cells stained with DAPI to visualize nuclei (left panels), phase contrast images (middle) and cells stained with specific antibodies to visualize indicated proteins (right panels).

Figure 8:
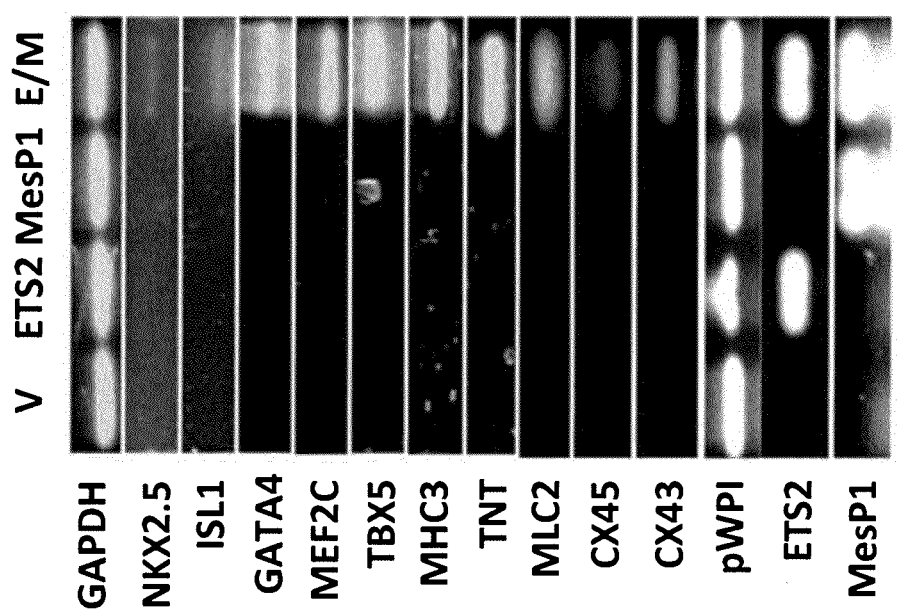
FIG. 8 shows that expression of NKX2.5, ISL1, GATA4, MEF2C, TBX5, MHC3, TNT, MLC2, CX43 and CX45, detected using RT-PCR, was only induced by the combination of ETS2 and Mesp1. Neither ETS2 or Mesp1 alone are capable of inducing these cardiogenic genes in NHDFs.

FIG. 8 shows that the MesP1 infection of EPS cells induces de novo cardiac progenitor program in cell that were originally NHDFs. Cardiac progenitor cells post-aggregation were plated for a week and then taken for RNA isolation. RNA was transcribed using MMLV reverse transcriptase, and PCR amplification for 30 cycles was performed for GAPDH, NKX2.5, ISL1, GATA4, MEF2C, TBX5, MHC3, TNT, MLC2, CX43 and CX45 (refer to Table 1 for primer sets), using LA-16 polymerase mix.

FIG. 8 shows that in EPS cells grown for 4 weeks, aggregated and plated for 7 days, no transcripts were observed for markers of early heart development by RT-PCR. Similarly, no appreciable expression of the early heart development markers was detected after infection of NHDFs with Mesp1 alone. However, Mesp1 addition to EPS cells induced robust expression of cardiac mesoderm progenitor markers including NKX2.5, ISL1, GATA4, MEF2C, TBX5, and cardiac contractile protein gene expression including alpha MHC and troponin T.

Figure 9:
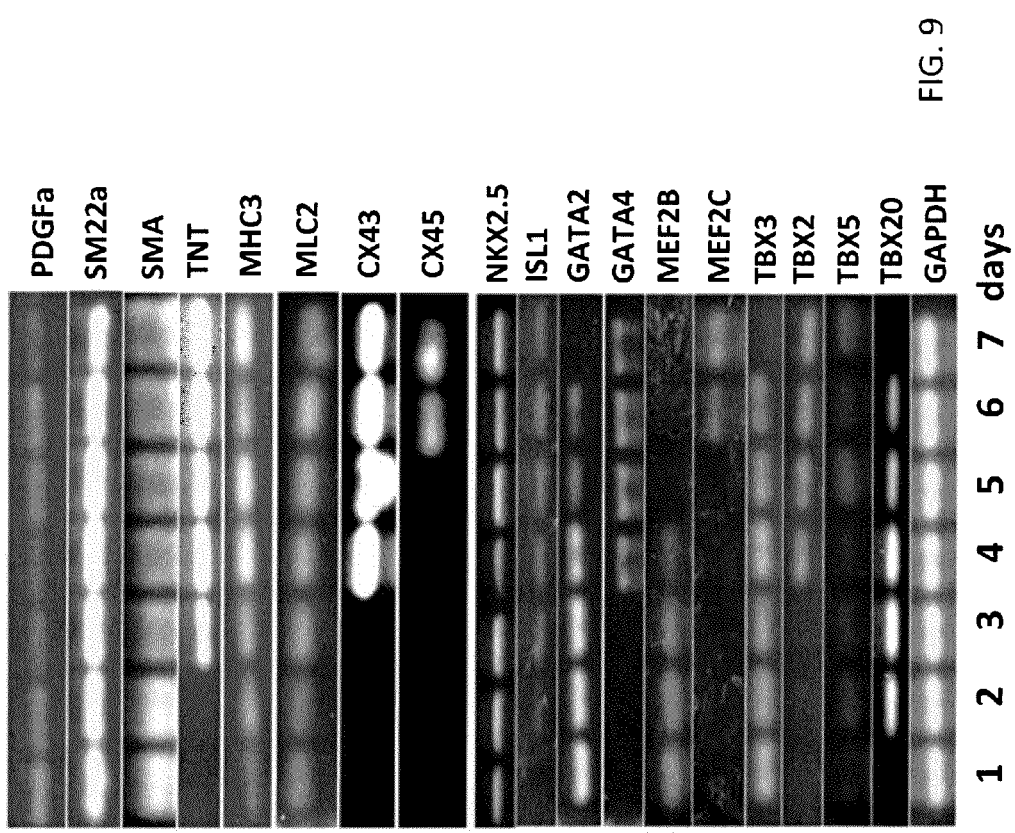
FIG. 9 shows induction of sequential de novo cardiac progenitor program. NHDFs were infected with ETS2 lentivirus, grown for 4 weeks, infected with Mesp1 lentivirus and cultured for 7 days, then aggregated by the hang-drop procedure and plated on a gelatin-coated dish.

FIG. 9 shows that the MesP1 infection of EPS cells induced sequential de novo cardiac progenitor program as determined by RT-PCR. NHDF-P3 cells were infected with ETS2 lentivirus, grown for 4 weeks, then infected with Mesp1 lentivirus, aggregated and plated for 7 days. RNA was isolated daily and analyzed by RT-PCR for expression of cardiogenic genes.

Figure 10:
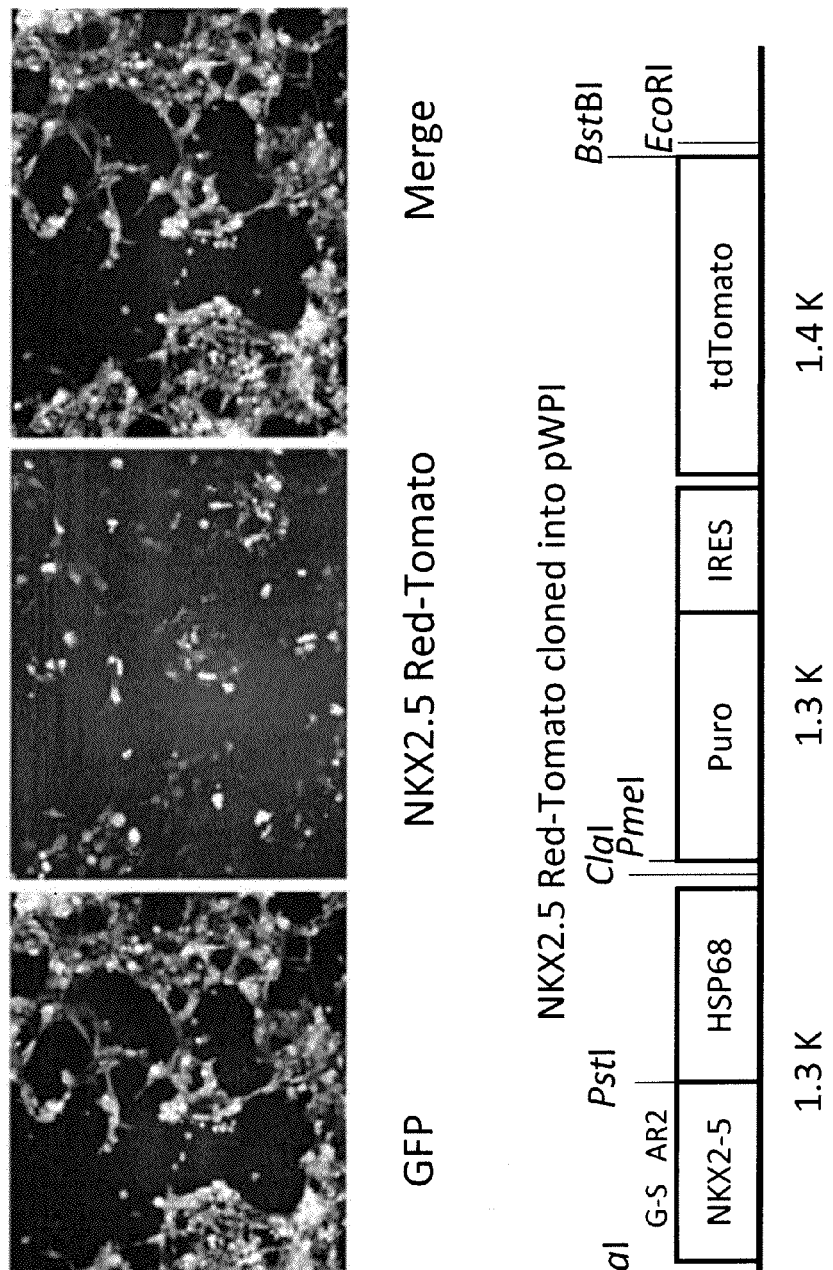
FIG. 10 shows activation of cardiac progenitor program gene expression, measured by fluorescence of the reporter protein Red-Tomato which is expressed only when the cardiac progenitor factor NKX2.5 is expressed. The fluorescent colors (colors not shown in the figures) are as follows: GFP (green), Red (red), a mixture of the two colors is observed in the "merge" panel.

FIG. 10 shows that the MesP1 infection of EPS cells induced de novo cardiac program gene expression as shown by the appearance of Red Tomato fluorescence staining from the reporter construct NKX2.5-Red Tomato. NKX2.5/Smad/GATA enhancer, which is activated in cardiac progenitors, was linked to the minimal HSP68 promoter adjacent to the puromycin resistance gene and an IRES sequence and the powerful reporter td-Tomato (cDNA was a gift from Dr. R. Tsien, University of California, San Diego). As shown above, GFP staining resulted from ETS2 and Mesp1 lentivirus infection of NHDFs. The Red Tomato fluorescence is consistent with the ETS2/Mesp1 driven conversion to cardiac progenitors by the induction of NKX2.5 gene expression. Note the appearance of many triangular and rectangular appearing cells that are highly similar in shape to cardiac myocytes.

Figure 11:
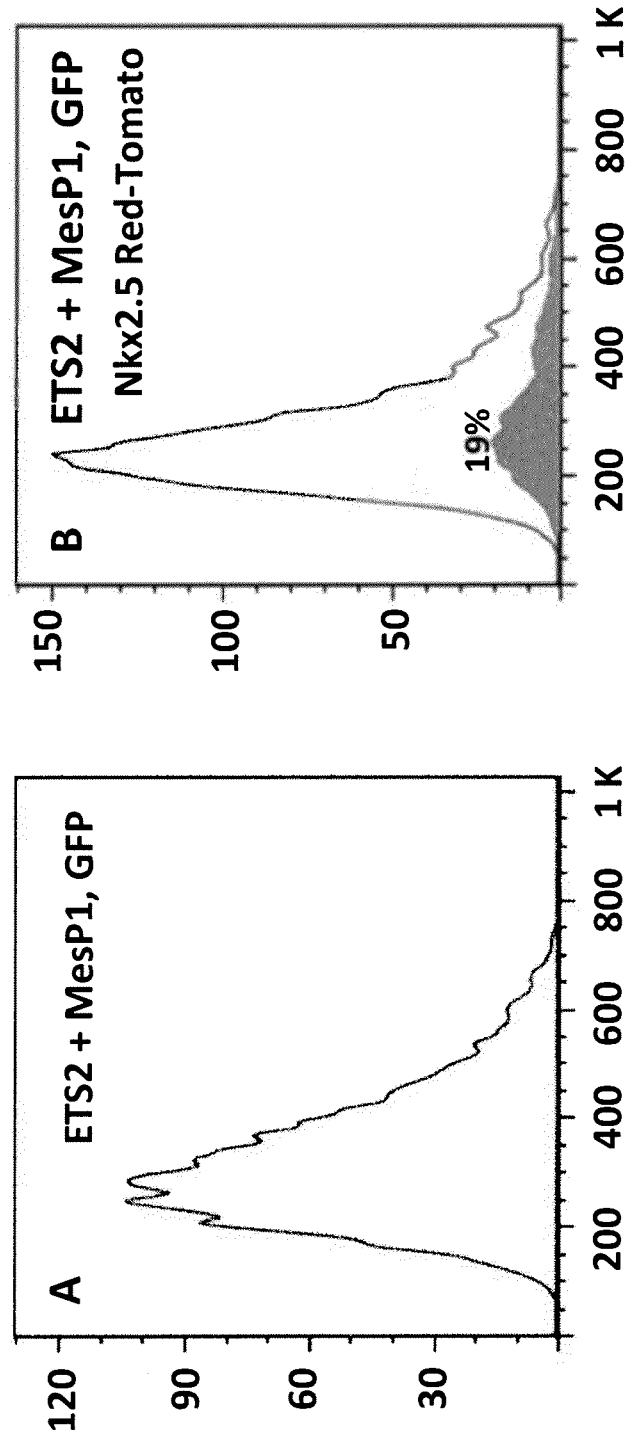
FIG. 11 shows flow cytometry of cardiac progenitor cells obtained from NHDFs by infection with ETS2 and Mesp1 lentivectors and sorted for either GFP or GFP and reporter protein Red-Tomato.

FIG. 11, Panel A shows a summary of FACS sorting of cardiac progenitor cells obtained from sequential treatment of NHDFs with ETS2 lentivirus and then of the resultant EPS cells with Mesp1 lentivirus. Flow cytometry was done using a BD Biosciences LSR II analyzer. Confluent colony-forming cells were dissociated by trypsin, washed with PBS and diluted to a concentration of $5 \times 10^6$ cells/ml PBS in 8 samples. Panel A shows GFP stained cells accounting for the total lentivirus infection, since each virus is GFP-tagged. Panel B shows that approximately 19% of the ETS2 and Mesp1 infected cells were both stained by GFP and Red-Tomato (shaded area). As evidenced by activation of a key cardiogenic reporter NKX2.5 Red-Tomato, ETS2 and Mesp1 efficiently convert NHDFs into cells with characteristics resembling cardiac progenitors.

Figure 12:
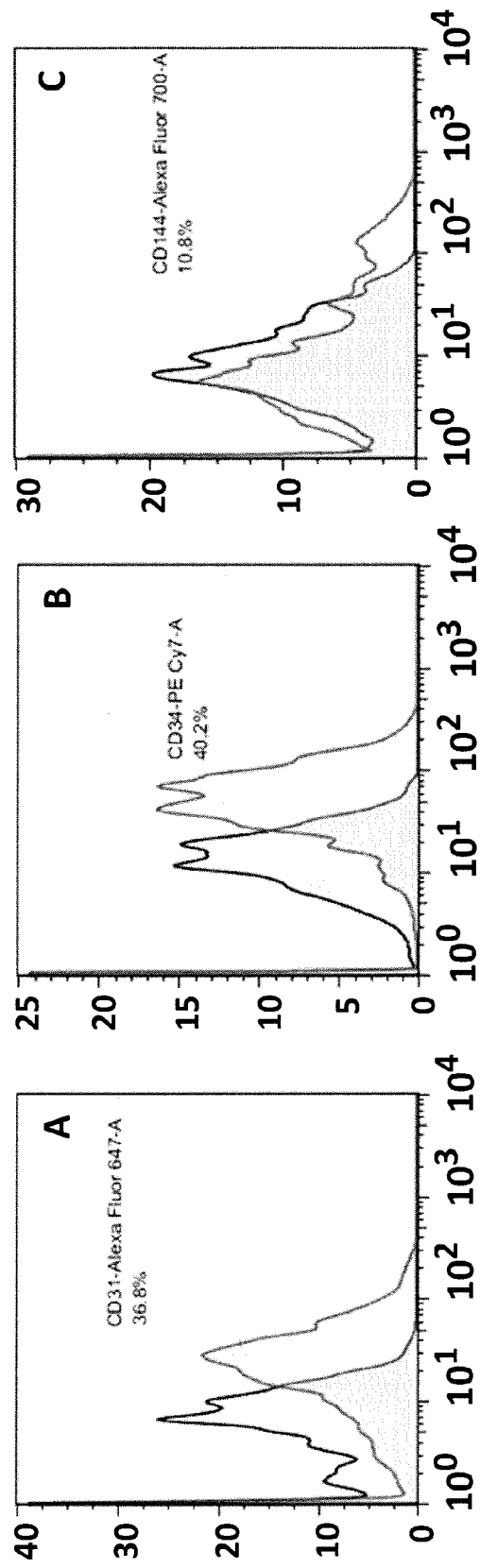
FIG. 12 shows display of endothelial and cardiac cell surface markers CD31, CD34 and CD144 in cardiac progenitor cells after 9 days in culture.

FIG. 12 shows that approximately 10 to 40% of ETS2 and Mesp1 infected NHDF cells display endothelial and cardiac cell surface markers, CD31. CD34 and CD144 after 9 days in culture. This is an additional line of evidence that ETS2 and Mesp1 efficiently converted NHDFs into cells with characteristics resembling embryonic endothelial and cardiac myocytes.

Example 7

Cardiac Properties of Reprogrammed Cells

Lentiviral transduction of a puromycin selectable system using a lentiviral cardiac-specific alpha-myosin heavy chain (alpha-MHC) promoter and enhancer linked to the puromycin resistance gene resulted in enrichment of the cardiac progenitor cells and subsequent observation of a rhythmic beating of the transduced cells, similar to that observed in cardiac myocytes.

A myosin heavy chain prometer driving the puromycin selectable gene construct was transduced into NHDFs which were then sequentially transduced with ETS2 and Mesp1. Cellular aggregates obtained during hang-drop embryoid body formation were then treated with 50 ug/ml puromycin to select cells resistant to puromycin and therefore having the active cardiac specific alpha-MHC promoter.

Figure 13:
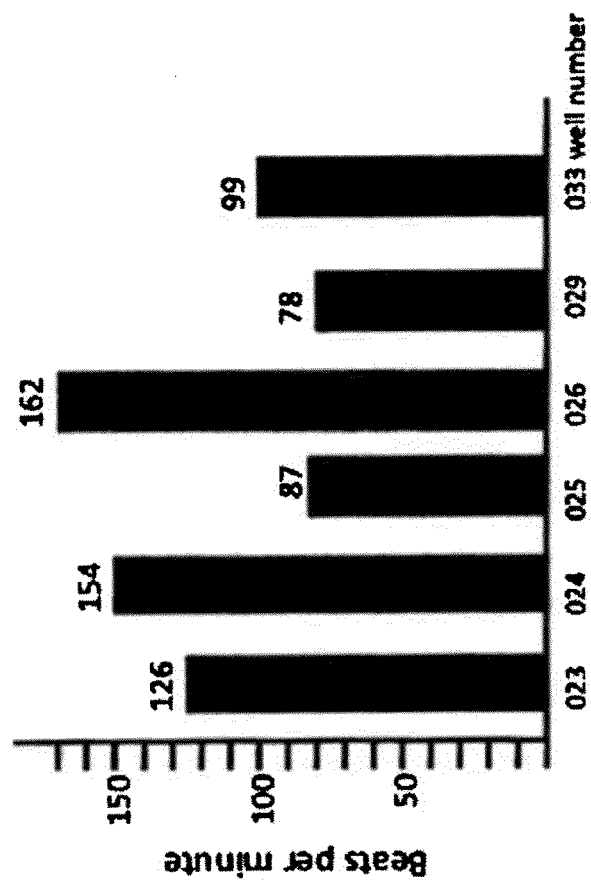
FIG. 13 shows the data on rhythmic beating in reprogrammed cardiac progenitor cells. EPS cells were infected with Mesp1 lentivirus, as well as with virus carrying a myosin heavy chain promoter driving the puromycin resistance gene. To select cardiac progenitor cells resistant to antibiotic, cells were treated with 50 ug/ml puromycin. After 9 days, rhythmic beating in the cell cultures was observed and captured by video microscopy and converted into MPEG videos. Beats per cultured aggregate per dish were counted for 20 sec and then multiplied by 3, resulting in beats per one minute. Three separate measurements were done per aggregate in a tissue culture dish or well.

After 9 days beating in the cell cultures was observed and captured using video microscopy and converted into MPEG videos. Beating per cultured aggregate per dish was counted for 20 sec and then multiplied by 3 for beats per one minute (FIG. 13). Three separate measurements were done per aggregate in a tissue culture dish or well.

Reprogramming of EPS cells with Mesp1 resulted in strong expression of cardiac progenitor genes as determined by RT-PCR and immunostaining. Additionally, flow cytometry showed that Mesp1 efficiently converted EPS cells into cells with surface markers CD31, CD34 and CD144 resembling human cardiac cells. Finally, rhythmic beating was observed in the cell cultures. This completed the conversion from skin fibroblasts to terminally differentiated cardiogenic cells.

REFERENCES CITED

The following references, to the extent that they provide exemplary procedural or other details supplementary to those set forth herein, are specifically incorporated herein by reference.

U.S. PATENT DOCUMENTS

U.S. Patent publication No. 2009/0227032 to S. Yamanaka.

NON-PATENT REFERENCES

Bergmann, O. et al. Evidence for cardiomyocyte renewal in humans. Science 324: 5923, 98-102, 2009.

Beh, J. et al. FoxF is essential for FGF-induced migration of heart progenitor cells in the ascidian Ciona intestinalis. Development 134: 3297-3305, 2007.

Davidson, B. Ciona intestinalis as a model for cardiac development. Semin. Cell Dev. Biol. 18: 16-26, 2007.

Davidson, B. and Levine, M. Evolutionary origins of the vertebrate heart: Specification of the cardiac lineage in Ciona intestinalis. Proc. Natl. Acad. Sci. USA 100: 11469-11473.

Imai, K. S., Satoh, N. and Satou, Y. A Twist-like bHLH gene is a downstream factor of an endogenous FGF and determines mesenchymal fate in the ascidian embryos. Development 130: 4461-4472, 2003.

Imai, K. S., Hino, K., Yagi, K., Satoh, N. and Satou, Y. Gene expression profiles of transcription factors and signaling molecules in the ascidian embryo: towards a comprehensive understanding of gene networks. Development 131: 4047-4058, 2004.

Kitajima, S. et al. MesP1 and MesP2 are essential for the development of cardiac mesoderm. Development 127: 3215-3226, 2000.

Moretti, A. et al. Multipotent embryonic isl+ progenitor cells lead to cardiac, smooth muscle and endothelial cell diversification. Cell 127: 1151-1165, 2006.

Park, I. H. et al. Reprogramming of human somatic cells to pluripotency with defined factors. Nature 451: 141-146, 2008.

Saga, Y. et al. MesP1 is expressed in the heart precursor cells and required for the formation of a single heart tube. Development 126:3437-3447, 1999.

Saga, Y., Kitajima, S, and Miyagawa-Tomita, SMesp1 expression is the earliest sign of cardiovascular development. Trends Cardiovasc Med. 10:345-352, 2000.

Takahashi, K. et al. Induction of pluripotent stem cells from adult human fibroblasts by defined factors. Cell 131:861-872, 2007.

Yu, J. Induced pluripotent stem cell lines derived from human somatic cells. Science 318:1917-1920, 2007.

---

What is claimed:

1. A method for preparing a cardiac progenitor cell, the method comprising:
   (a) transducing a somatic cell with an ETS2 reprogramming factor forming an ETS2 treated cell, wherein the ETS2 treated cell produces a pluripotent stem cell marker protein not present in the somatic cell; and
   (b) transducing the ETS2 treated cell with a Mesp1 reprogramming factor forming a cardiac progenitor cell, wherein the cardiac progenitor cell produces a cardiac cell marker protein neither expressed in the somatic cell nor in the ETS2 treated cell;
   wherein the somatic cell is a normal human dermal fibroblast cell.

2. The method of claim 1, wherein the ETS2 comprises the DNA sequence having SEQ ID NO:9.

3. The method of claim 1, wherein the Mesp1 comprises the DNA sequence having SEQ ID NO:6.

* * * * *